(12) United States Patent
Hayashi et al.

(10) Patent No.: US 9,006,253 B2
(45) Date of Patent: Apr. 14, 2015

(54) CRYSTAL OF 2-(3,4-DICHLOROBENZYL)-5-METHYL-4-OXO-3,4-DIHYDROTHIENO[2,3-D]PYRIMIDINE-6-CARBOXYLIC ACID

(71) Applicant: ASKA Pharmaceutical Co., Ltd., Tokyo (JP)

(72) Inventors: Hiroyuki Hayashi, Kawasaki (JP); Takayoshi Nakagawa, Kawasaki (JP); Koichi Miyazaki, Kawasaki (JP)

(73) Assignee: ASKA Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/226,505

(22) Filed: Mar. 26, 2014

(65) Prior Publication Data

US 2014/0235655 A1 Aug. 21, 2014

Related U.S. Application Data

(62) Division of application No. 13/700,935, filed as application No. PCT/JP2011/062513 on May 31, 2011, now Pat. No. 8,748,437.

(30) Foreign Application Priority Data

May 31, 2010 (JP) ................. 2010-125362

(51) Int. Cl.
*A61K 31/519* (2006.01)
*C07D 239/90* (2006.01)
*C07D 495/04* (2006.01)

(52) U.S. Cl.
CPC ............ *C07D 495/04* (2013.01); *A61K 31/519* (2013.01)

(58) Field of Classification Search
CPC ............................ A61K 31/519; C07D 239/90
USPC ....................................... 514/260.1; 544/278
See application file for complete search history.

(56) References Cited

U.S. PATENT DOCUMENTS

2009/0203703 A1 8/2009 Gotanda et al.
2010/0113484 A1 5/2010 Gotanda et al.

FOREIGN PATENT DOCUMENTS

CN          101198614 A    6/2008
CN          101557826 A    10/2009
WO       WO 2006/135080 A1    12/2006
WO       WO 2001/152411 A1    12/2011

OTHER PUBLICATIONS

Hackam et al., *Jama*, 296(14): 1731-1732 (2006).
Hirayama, Noriaki, *Yuki Kagoubutu Kessho Sakusei Handbook* (Handbook for Preparing Crystal of Organic Compound), Maruzen Co., Ltd., chapter 4, pp. 57-79 (Jul. 25, 2008).
Jordan et al., *Nature Reviews: Drug Discovery*, 2: 205-213 (2003).
Japanese Patent Office, International Search Report in International Patent Application No. PCT/JP2011/062513 (Jul. 26, 2011).
International Bureau of WIPO, International Preliminary Report on Patentability in International Patent Application No. PCT/JP2011/062513 (Jan. 8, 2013).

*Primary Examiner* — Douglas M Willis
(74) *Attorney, Agent, or Firm* — Leydig, Voit & Mayer, Ltd.

(57) ABSTRACT

The invention provides a crystal of 2-(3,4-dichlorobenzyl)-5-methyl-4-oxo-3,4-dihydrothieno[2,3-d]pyrimidine-6-carboxylic acid (which has the chemical structure shown below) and a mixed crystal comprising such a crystal.

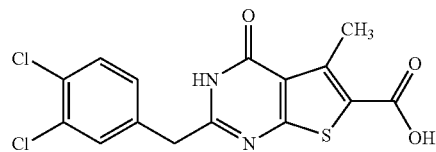

The invention also provides methods of producing such crystals, pharmaceutical compositions comprising such crystals, and methods of modulating phosphodiesterase-9 activity and treating disorders such as overactive bladder syndrome by administration of an effective amount of the crystals.

15 Claims, 16 Drawing Sheets

CRYSTAL OF 2-(3,4-DICHLOROBENZYL)-5-METHYL-4-OXO-3,4-DIHYDROTHIENO[2,3-D]PYRIMIDINE-6-CARBOXYLIC ACID

CROSS-REFERENCE TO RELATED APPLICATIONS

This patent application is a divisional of copending U.S. patent application Ser. No. 13/700,935, filed on Nov. 29, 2012, which is the U.S. national phase of International Patent Application No. PCT/JP2011/062513, filed on May 31, 2011, which claims the benefit of Japanese Patent Application No. 2010-125362, filed on May 31, 2010, which are incorporated by reference in their entireties herein.

TECHNICAL FIELD

The present invention relates to a crystal of 2-(3,4-dichlorobenzyl)-5-methyl-4-oxo-3,4-dihydrothieno[2,3-d]pyrimidine-6-carboxylic acid (hereinafter to be referred to as "compound A") useful as a therapeutic drug for dysuria and the like, a medicament containing the crystal and a production method of the crystal.

BACKGROUND ART

Compound A is a compound described in WO 2006/135080 (see patent document 1), which has a high PDE9 inhibitory action as well as a mild PDE5 inhibitory action, and is useful for the treatment or procedure of dysuria and the like.

However, patent document 1 does not clearly show concrete properties of the obtained compound A and does not describe or suggest the presence of crystal polymorph.

DOCUMENT LIST

Patent Document patent document 1: WO 2006/135080

BRIEF SUMMARY OF THE INVENTION

Problems to be Solved by the Invention

The problem of the present invention is to provide a crystal of compound A.

Means of Solving the Problems

In view of the above-mentioned problem, the present inventors have studied various aspects of crystallization of compound A, and successfully obtained novel amorphous form (amorphous), solvate crystals and unsolvated crystals of compound A.

Particularly, they have found that an unsolvated crystal showing particular property data (Form I crystal and Form II crystal to be mentioned later) cannot be obtained by general crystallization methods such as recrystallization and the like using various organic solvents, but can unexpectedly be produced by a convenient method including heating in an aqueous suspension for a given time.

This method can be performed as a work-up in the final step of industrial production, with no need to separately include a burdensome step of a crystallization step. In addition, the obtained crystal is superior in filterability. Thus, the method is suitable for large-scale production from the aspects of operability and cost. Furthermore, they have found that these crystals have superior property as a medicament, which resulted in the completion of the present invention.

Accordingly, the present invention relates to

[1] a crystal of 2-(3,4-dichlorobenzyl)-5-methyl-4-oxo-3,4-dihydrothieno[2,3-d]pyrimidine-6-carboxylic acid having an X-ray powder diffraction pattern showing diffraction peaks at diffraction angles 2θ of 6.7±0.2°, 8.3±0.2°, 8.9±0.2°, 14.0±0.2°, 14.8±0.2° and 26.4±0.2° in X-ray powder diffraction spectrum;

[2] the crystal of the above-mentioned [1], showing an endothermic peak having a peak top temperature of 362±5° C. in differential scanning calorimetry (DSC);

[3] a crystal of 2-(3,4-dichlorobenzyl)-5-methyl-4-oxo-3,4-dihydrothieno[2,3-d]pyrimidine-6-carboxylic acid, having an X-ray powder diffraction pattern showing diffraction peaks at diffraction angles 2θ of 7.3±0.2°, 11.2±0.2°, 13.3±0.2°, 17.0±0.2°, 25.5±0.2° and 27.5±0.2° in X-ray powder diffraction spectrum;

[4] the crystal of the above-mentioned [3], showing an endothermic peak having a peak top temperature of 342±5° C. in differential scanning calorimetry (DSC);

[5] the crystal of any of the above-mentioned [1] to [4], which is an unsolvated and unhydrated crystal;

[6] a mixed crystal comprising the crystal of the above-mentioned [1] or [2], and the crystal of the above-mentioned [3] or [4];

[7] a medicament comprising the crystal of any of the above-mentioned [1] to [6] as an active ingredient;

[8] a pharmaceutical composition comprising the crystal of any of the above-mentioned [1] to [6] and a pharmaceutically acceptable carrier;

[9] the medicament of the above-mentioned [7], which is a PDE9 inhibitor;

[10] the medicament of the above-mentioned [7], which is a therapeutic agent for overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary diseases, ischemic heart diseases, hypertension, angina, myocardial infarction, arteriosclerosis, thrombosis, embolism, and type I diabetes or type II diabetes;

[11] a method of producing the crystal of any of claims 1 to 6, comprising a step of heating an aqueous suspension of 2-(3,4-dichlorobenzyl)-5-methyl-4-oxo-3,4-dihydrothieno[2,3-d]pyrimidine-6-carboxylic acid;

[12] a method of producing the crystal of the above-mentioned [1] or [2], comprising a step of heating an aqueous suspension of 2-(3,4-dichlorobenzyl)-5-methyl-4-oxo-3,4-dihydrothieno[2,3-d]pyrimidine-6-carboxylic acid at not less than 40° C. and less than 50° C. for 1 to 96 hr, not less than 50° C. and less than 60° C. for 0.5 to 32 hr, not less than 60° C. and less than 70° C. for 0.5 to 24 hr, not less than 70° C. and less than 80° C. for 0.1 to 12 hr, not less than 80° C. and less than 90° C. for 0.05 to 6 hr, or not less than 90° C. and not more than 100° C. for 0.01 to 3 hr;

[13] a method of producing the crystal of the above-mentioned [3] or [4], comprising a step of heating an aqueous suspension of 2-(3,4-dichlorobenzyl)-5-methyl-4-oxo-3,4-dihydrothieno[2,3-d]pyrimidine-6-carboxylic acid at not less than 60° C. and less than 70° C. for 144 hr or more, not less than 70° C. and less than 80° C. for 25 hr or more, not less than 80° C. and less than 90° C. for 23 hr or more, or not less than 90° C. and not more than 100° C. for 16 hr or more;

[14] the production method of any of the above-mentioned [11] to [13], comprising heating an aqueous suspension obtained by neutralizing or acidifying an aqueous alkaline solution of 2-(3,4-dichlorobenzyl)-5-methyl-4-oxo-3,4-dihydrothieno[2,3-d]pyrimidine-6-carboxylic acid; and the like.

Effect of the Invention

According to the present invention, a novel unsolvated crystal of compound A can be obtained. This crystal can be produced by a convenient method suitable for industrial large-scale production. In addition, the obtained crystal can be easily filtered as compared to amorphous form, and is suitable for industrial large-scale production. Furthermore, the crystal of the present invention is also suitable as an active ingredient of a medicament in stability, solubility, absorbability and the like.

DETAILED DESCRIPTION OF THE INVENTION

Figure 1:
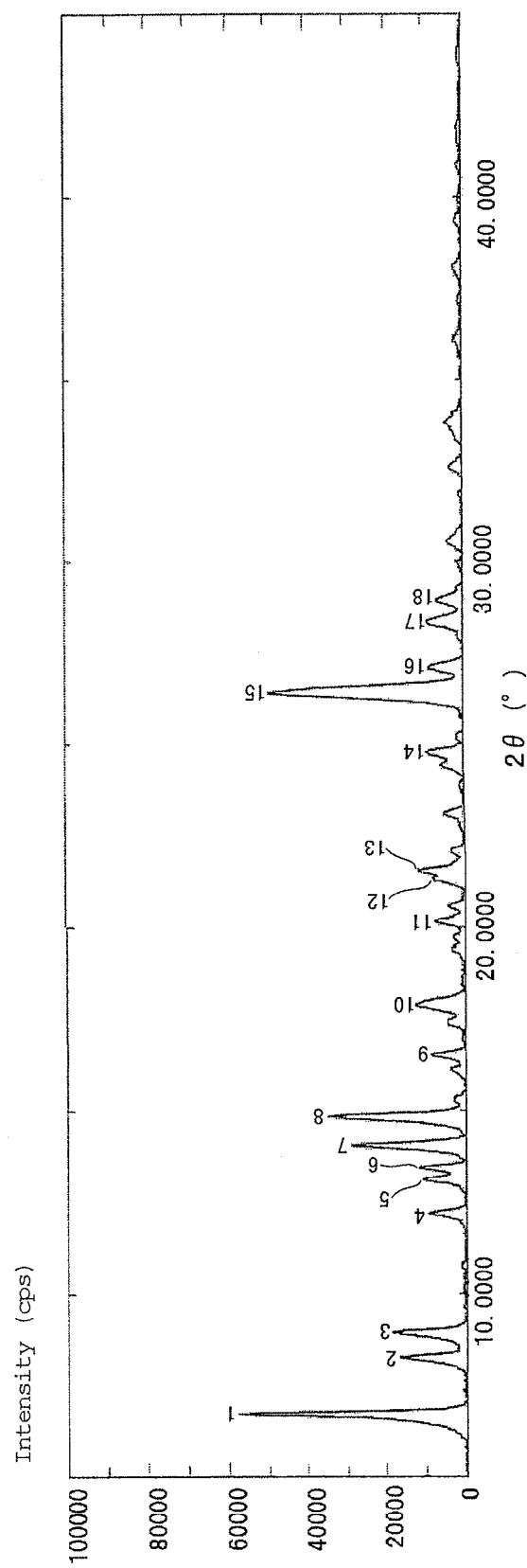
FIG. 1 shows an X-ray powder diffraction pattern of Form I crystal of compound A (Example 1).

A production method of compound A is disclosed in Example 36-a) of patent document 1, wherein production in the same manner as in Example 1 is described. In Example 1 of the patent document 1, it is described that an ester compound is ester-hydrolyzed by heating under reflux in an aqueous alkaline solution to give carboxylic acid, which is acidified with dilute hydrochloric acid, and the precipitated crystals are collected by filtration. However, compound A having what property was obtained in Example 36-a) is not clearly shown.

Thus, the present inventors first conducted a replication study of the above-mentioned experiment. Compound A was produced by a method similar to that specifically disclosed in Example 1 of patent document 1. As a result, although crystals were precipitated in said Example 1, an aggregate was in fact suspended. When the aggregate was filtrated by suction, the filter was clogged, and the filtration took an extremely long time. The aggregate was measured by X-ray powder diffraction, but a clear peak showing the presence of crystal was not found, which has clarified that this production method only affords a simple aggregate (amorphous form) or a powder having low crystallinity, rather than a crystal.

Amorphous forms generally have low stability to light and heat, and have defects in that they are difficult to handle because of being glassy and the like. In addition, amorphous forms tend to allow presence of impurity as compared to crystal. As mentioned above, moreover, since compound A obtained in an amorphous form causes clogging during filtration by suction, it is not suitable for industrial large-scale production. To use compound A as a pharmaceutically active ingredient, and for industrial large-scale production, production of compound A in a crystal form is desired.

Therefore, the present inventors have tried crystallization of compound A using various solvents. As a result, pseudo crystals of various organic solvent solvates of compound A were obtained, but a crystal free of an organic solvent could not be obtained.

In general, crystal of solvate often has problems of stability such as easy transformation due to dissociation of solvent and the like, as compared to unsolvated crystals and, unless a stable crystal such as hydrate crystal and the like is obtained, difficulty of handling as a medicament is feared. In addition, since a substantial amount of organic solvent is contained, the safety of the solvent itself should also be considered, and various difficulties are expected in the development as a medicament.

Furthermore, the present inventors have conducted various studies in an attempt to obtain an unsolvated crystal, and unexpectedly found that a novel unsolvated crystal of compound A can be produced by a convenient operation of heating an aqueous suspension of compound A for a given time, and further, the obtained crystal can be easily filtered as compared to amorphous forms and is suitable for industrial large-scale production.

Furthermore, they have found that two novel unsolvated crystals of compound A (hereinafter to be referred to as Form I crystal and Form II crystal) and a mixed crystal thereof can be produced separately by appropriately adjusting the heating temperature and duration.

Moreover, the thus-obtained Form I crystal and Form II crystal have preferable properties as a medicament in terms of solubility, stability, absorbability and the like.

The detail is explained in the following.

1. Production of Amorphous Compound A

An amorphous compound A can be obtained as a precipitated aggregate by neutralizing or acidifying an aqueous alkaline solution of compound A with an acid. Examples of the method for obtaining the aggregate from water suspension include collection by filtration, centrifugation, a method including precipitation and decanting supernatant and the like. Of these, collection by filtration is convenient and preferable. However, this method has a room for improvement for application to industrial production since it requires an extremely long time due to the clogging of filter, and shows poor dewatering.

The aqueous alkaline solution of compound A may contain an organic solvent miscible with water. Examples of the organic solvent include alcohols (e.g., methanol, ethanol, propanol, isopropanol etc.), amides (e.g., N,N-dimethylformamide, N,N-dimethylacetamide etc.), ethers (e.g., tetrahydrofuran, dioxane etc.) and the like. The amount of the solvent to be used is preferably 0.01- to 0.1-fold (v/v) relative to water.

The aqueous alkaline solution of compound A can be prepared by dissolving compound A or a salt thereof (e.g., sodium salt, potassium salt etc.) in an aqueous alkaline solution. Examples of the aqueous alkaline solution include aqueous solutions of sodium hydroxide, potassium hydroxide, potassium carbonate and the like. While the amount of alkali to be used can be about 1 to 5 mol per 1 mol of compound A, 2 mol or more is preferable, and 2 to 2.4 mol is particularly preferable. When the amount of alkali to be used is less than this range, compound A is not easily dissolved in an aqueous alkaline solution.

In addition, as an aqueous alkaline solution of compound A, a reaction solution obtained by alkaline hydrolysis of an ester form of compound A (e.g., $C_{1-6}$ alkyl ester form of compound A such as ethyl 2-(3,4-dichlorobenzyl)-5-methyl-4-oxo-3,4-dihydrothieno[2,3-d]pyrimidine-6-carboxylate and the like produced in Production Example 10 of patent document 1) may be used.

Hydrolysis of an ester form of compound A can be performed according to a method known per se, for example, suspending or dissolving an ester form of compound A in water or a mixed solvent of alcohols such as methanol, ethanol, isopropanol and the like added with water, in the presence of alkali such as sodium hydroxide, potassium hydroxide, potassium carbonate and the like at 0° C. to the refluxing temperature of the reaction mixture, preferably within the range of room temperature to the refluxing temperature of the reaction mixture. While the ratio of alkali to be used relative to an ester form of compound A is not particularly limited, alkali can be generally used within the range of about 1 to 20 mol per 1 mol of an ester form of compound A.

The concentration of the aqueous alkaline solution of compound A is preferably about 0.5 to 2 mol/L.

Examples of the acid to be used for neutralization or acidification of an aqueous alkaline solution of compound A include hydrochloric acid, sulfuric acid, nitric acid, phosphoric acid, formic acid, acetic acid, oxalic acid and the like, with preference given to dilute hydrochloric acid.

For neutralization, an equivalent amount of an acid relative to the base contained in the aqueous alkaline solution only needs to be added. For acidification, the pH thereof is not particularly limited, but an acid is preferably added to adjust pH to about 5 to 7.

The precipitated aggregate is obtained by collection by filtration, centrifugation and the like, and washed and dried to give an amorphous compound A. When an amorphous aggregate is obtained by collection by filtration, the filter is easily clogged and the filtration takes time even when suctioned during filtration. Therefore, obtainment by collection by filtration is not suitable for industrial production.

2. Production Method of Form I Crystal and Form II Crystal

The Form I crystal and Form II crystal of compound A can be produced by heating an aqueous suspension of compound A for a given time.

The aqueous suspension of compound A may contain an organic solvent miscible with water. Examples of the organic solvent include alcohols (e.g., methanol, ethanol, propanol, isopropanol etc.) and the like. Since production of a crystal of the organic solvent solvate contained is feared, it is preferable to not contain an organic solvent.

The amount of the solvent to be used when an organic solvent is contained is preferably 0.001- to 0.3-fold (v/v) relative to water. When the amount of the organic solvent is greater than this range, production of a crystal of the organic solvent solvate is feared.

While the form of compound A in the suspension in the above-mentioned "aqueous suspension of compound A" is not particularly limited, an amorphous form is preferable.

The aqueous suspension of compound A can be prepared by adding compound A to water or a mixed solvent of water and an organic solvent, and stirring them.

Alternatively, preferably, the suspension wherein an amorphous compound A is precipitated by adding an acid to an aqueous alkaline solution of compound A, in the production method of the amorphous compound A explained in the above-mentioned 1., can be used as an aqueous suspension of compound A.

Particularly preferably, a suspension wherein an amorphous compound A is precipitated, which is obtained by adding an acid to a reaction solution obtained by alkaline hydrolysis of an ester form of compound A, can be used as an aqueous suspension of compound A. This method is particularly advantageous for industrial production since, in alkaline hydrolysis of an ester form, which is the final step of industrial production of compound A in this method,
Form I crystal and Form II crystal of compound A can be prepared in one pot by work-up, without once taking out compound A from the reaction container.

In the heating conditions of the aqueous suspension of compound A, Form I crystal and Form II crystal, or a mixed crystal thereof can be produced separately by appropriately adjusting heating duration and heating temperature. That is, by heating an aqueous suspension of compound A in a given temperature range for a given time, Form I crystal can be first produced. Furthermore, by heating at a higher temperature and/or for a longer time, Form I crystal is converted to Form II crystal, whereby Form II crystal or a mixed crystal of Form I crystal and Form II crystal can be obtained.

In the following, heating an aqueous suspension of compound A in a given temperature range and for a given time is referred to as "maturation".

During maturation, an aqueous suspension may be left standing, or can be, for example, stirred, shaken or convected, with preference given to stirring.

When Form I crystal is produced by maturation of an aqueous suspension of compound A, the relationship between maturation temperature and time is that a lower temperature requires maturation for a comparatively long time, and a higher temperature can afford Form I crystal by maturation for a comparatively short time.

Specifically, Form I crystal can be obtained by setting the maturation temperature and time to, for example, not less than 40° C. and less than 50° C. and 1 to 96 hr (more preferably 8 to 48 hr), not less than 50° C. and less than 60° C. and 0.5 to 32 hr (more preferably 4 to 24 hr), not less than 60° C. and less than 70° C. and 0.5 to 24 hr (more preferably 2 to 6 hr), not less than 70° C. and less than 80° C. and 0.1 to 12 hr (more preferably 1.5 to 4 hr), not less than 80° C. and less than 90° C. and 0.05 to 6 hr (more preferably 0.5 to 3 hr), not less than 90° C. and not more than 100° C. and 0.01 to 3 hr (more preferably 0.1 to 2 hr) or the like. In consideration of the production efficiency, crystallinity, possibility of mixing of other crystal form and the like, of these, maturation at not less than 70° C. and less than 80° C. for 0.1 to 12 hr is preferable, and maturation at not less than 70° C. and less than 80° C. for 1.5 to 4 hr is particularly preferable. In some cases when a higher temperature (e.g., not less than 90° C. and not more than 100° C.) is used, maturation is completed during temperature rise, and Form I crystal is obtained at the time point when said temperature is reached.

In another embodiment, Form I crystal can be obtained by setting the maturation temperature and time to, for example, not less than 40° C. and less than 50° C. and 1 to 96 hr (more preferably 8 to 48 hr), not less than 50° C. and less than 60° C. and 0.5 to 48 hr (more preferably 4 to 24 hr), not less than 60° C. and less than 70° C. and 0.5 to 24 hr (more preferably 2 to 6 hr), not less than 70° C. and less than 80° C. and 0.1 to 12 hr (more preferably 1.5 to 4 hr), not less than 80° C. and less than 90° C. and 0.05 to 6 hr (more preferably 0.5 to 3 hr), not less than 90° C. and not more than 100° C. and 0.01 to 3 hr (more preferably 0.1 to 2 hr) or the like.

In a third embodiment, Form I crystal can also be obtained by setting the maturation temperature and time to, for example, not less than 40° C. and less than 50° C. and 1 to 96 hr (more preferably 8 to 48 hr), not less than 50° C. and less than 60° C. and 0.5 to 32 hr (more preferably 4 to 24 hr), not less than 60° C. and less than 70° C. and 0.5 to 24 hr (more preferably 2 to 6 hr), not less than 70° C. and less than 80° C. and 0.1 to 12 hr (more preferably 1.5 to 4 hr), not less than 80° C. and less than 90° C. and 0.05 to 6 hr (more preferably 0.5 to 3 hr), not less than 90° C. and not more than 100° C. and 0.01 to 4 hr (more preferably 0.1 to 2 hr) or the like.

The maturation time to obtain Form I crystal may vary somewhat depending on the difference in the experiment conditions.

Furthermore, by heating at a higher temperature and/or for a longer time than the above-mentioned ranges, Form I crystal is converted to Form II crystal, or amorphous form is converted to Form II crystal via Form I crystal, whereby Form II crystal can be obtained.

Specifically, Form II crystal can be obtained by setting the maturation temperature and time to, for example, not less than 60° C. and less than 70° C. and 144 hr or more (more preferably not less than 155 hr), not less than 70° C. and less than 80° C. and 25 hr or more (more preferably not less than 30 hr), not less than 80° C. and less than 90° C. and 23 hr or more (more preferably not less than 25 hr), not less than 90° C. and not more than 100° C. and 16 hr or more (more preferably not less than 20 hr) or the like. Of these, maturation at not less than 90° C. and not more than 100° C. for 16 hr or more is preferable, and maturation at not less than 90° C. and not more than 100° C. for 20 hr or more is particularly preferable.

In another embodiment, Form II crystal can be obtained by setting the maturation temperature and time to, for example, not less than 60° C. and less than 70° C. and 70 hr or more (more preferably not less than 80 hr), not less than 70° C. and less than 80° C. and 25 hr or more (more preferably not less than 30 hr), not less than 80° C. and less than 90° C. and 12 hr or more (more preferably not less than 15 hr), not less than 90° C. and not more than 100° C. and 5 hr or more (more preferably not less than 8 hr) or the like. Of these, maturation at not less than 90° C. and not more than 100° C. for 5 hr or more is preferable, and maturation at not less than 90° C. and not more than 100° C. for 8 hr or more is particularly preferable.

While the upper limit of the maturation time for obtaining Form II crystal is not particularly limited, maturation may be further continued for about 1 to 2 hr from the lower limit of the above-mentioned maturation time.

In addition, the maturation time for obtaining Form II crystal may vary somewhat depending on the experiment conditions thereof.

A mixed crystal of Form I crystal and Form II crystal can be obtained by discontinuing the maturation of an aqueous suspension of compound A during conversion of Form I crystal to Form II crystal.

A mixed crystal of Form I crystal and Form II crystal at a desired mixing ratio can be obtained by, for example, sampling within the range of further maturation conditions after production of Form I crystal, and monitoring the amount ratio of Form I crystal and Form II crystal by X-ray powder diffraction, DSC and the like.

After producing Form I crystal and/or Form II crystal by maturation under the above-mentioned respective conditions, the crystals can be collected by filtration by a general method, washed with water and the like as necessary, and further dried.

As an analysis method of the thus-obtained crystals, X-ray powder diffraction is preferable. In addition, infrared absorption spectrum, solid-state NMR, differential scanning calorimetry (DSC), thermogravimetry/differential thermal analysis (TG-DTA) and the like may be used in combination. While measurement conditions of these are not particularly limited, measurement under the measurement conditions described in the present specification is preferable.

Each spectrum obtained by such analysis methods has a certain measurement error caused by the nature thereof. A crystal having a peak with a spectrum error within the error range is also encompassed in the scope of the present invention. For example, in the case of a measurement by X-ray powder diffraction, a crystal having a peak within the error range of ±0.2° at diffraction angles 2θ is contained in the present invention.

An error range of ±5° C. is acceptable in differential scanning calorimetry (DSC), and an error range of ±0.5% is acceptable in infrared absorption spectrum.

The Form I crystal of the present invention shows an X-ray powder diffraction pattern having characteristic diffraction peaks at diffraction angles 2θ of 6.7°, 8.3°, 8.9°, 14.0°, 14.8° and 26.4° (each ±0.2°), using CuKα radiation as X-ray, preferably an X-ray powder diffraction pattern having diffraction peaks at 6.7°, 8.3°, 8.9°, 13.1°, 13.4°, 14.0°, 14.8°, 17.9°, 21.6° and 26.4° (each ±0.2°).

In addition, Form I crystal of the present invention has an endothermic peak showing a peak top temperature of about 362° C. (±5° C.) in differential scanning calorimetry (DSC), and an infrared absorption spectrum pattern showing absorption peaks at 1713, 1673, 1643, 1590, 1532, 1421, 1265, 1214 and 1034 cm$^{-1}$ (each ±0.5%) in infrared absorption spectrum (paste method).

The Form II crystal of the present invention shows an X-ray powder diffraction pattern having characteristic diffraction peaks at diffraction angles 2θ of 7.3°, 11.2°, 13.3°, 17.0°, 25.5° and 27.5° (each)±0.2°, using CuKα radiation as X-ray, preferably an X-ray powder diffraction pattern having diffraction peaks at 7.3°, 11.2°, 13.3°, 17.0°, 22.4°, 23.1°, 25.5° and 27.5° (each ±0.2°).

The Form II crystal of the present invention has an endothermic peak having a peak top temperature of about 342° C. (±5° C.) in differential scanning calorimetry (DSC), and shows an infrared absorption spectrum pattern having absorption peaks at 1706, 1669, 1649, 1584, 1530, 1283, 1271, 1260, 1215, 1203, 1137, 1033 cm$^{-1}$ (each ±0.5%) in infrared absorption spectrum (paste method).

3. Production of Solvate Crystal of Compound A

Solvate crystal of compound A can be prepared by a cooling method (slow cooling) or a heating suspension stirring method using various organic solvents. Specific procedures of each method are as described below.

(Cooling Method)

Compound A is dissolved by heating in a soluble organic solvent, and cooled slowly to room temperature to allow precipitation of crystals.

(Heating Suspension Stirring Method)

Compound A is suspended in a poorly soluble organic solvent, and the mixture is suspended and stirred with heating.

To be specific, an isopropanol solvate can be obtained by a heating suspension stirring method of isopropanol, a dimethylacetamide solvate can be obtained by a heating suspension stirring method of dimethylacetamide-acetone, a dimethylformamide solvate can be obtained by a cooling method of dimethylformamide-water, a 1,3-dimethyl-2-imidazolidinone solvate can be obtained by a cooling method of 1,3-dimethyl-2-imidazolidinone, and an N-methylpyrrolidone solvate can be obtained by a cooling method of N-methylpyrrolidone, as respective pseudo crystal forms. The detail of the production method of each solvate crystal and the property data of the obtained solvate crystals are as described in the below-mentioned Reference Examples.

Form I crystal and Form II crystal of the present invention, and a mixed crystal thereof (hereinafter to be referred to as the crystal of the present invention) have a superior PDE9 inhibitory action and a mild PDE5 inhibitory action, and is useful as a medicament for the treatment and procedure of diseases wherein decomposition of cGMP due to PDE9 is involved; for example, overactive bladder syndrome, pollakiuria, urinary incontinence, dysuria in benign prostatic hyperplasia, neurogenic bladder, interstitial cystitis, urolithiasis, benign prostatic hyperplasia, erectile dysfunction, cognitive impairment, neuropathy, Alzheimer's disease, pulmonary hypertension, chronic obstructive pulmonary diseases, ischemic heart diseases, hypertension, angina, myocardial infarction, arteriosclerosis, thrombosis, embolism, type I diabetes, type II diabetes and the like.

Use of compound A as an agent for the treatment or procedure of dysuria and the like is disclosed in detail in patent document 1, and similarly, the crystal of the present invention can be administered orally or parenterally (e.g., intramuscular injection, intravenous injection, rectal administration, transdermal administration etc.) for the treatment, procedure and the like of dysuria and the like in human and other mammals. All disclosures of patent document 1 are encompassed in full in the disclosure of the present specification as reference.

The crystal of the present invention can be formulated, together with non-toxic excipients, into any preparation form such as solid (e.g., tablet, hard capsule, soft capsule, granule, powder, fine granule, pill, troche etc.); semi-solid (e.g., suppository, ointment etc.); or liquid (e.g., injection, emulsion, suspension, lotion, spray etc.). Particularly, a solid preparation is preferable.

Examples of the non-toxic excipients usable for the above-mentioned preparations include starch, gelatin, glucose, lactose, fructose, maltose, magnesium carbonate, talc, magnesium stearate, methyl cellulose, carboxymethyl cellulose and salts thereof, gum Arabic, polyethylene glycol, p-hydroxybenzoic acid alkyl ester, syrup, ethanol, propylene glycol, vaseline, Carbowax, glycerine, sodium chloride, sodium sulfite, sodium phosphate, citric acid and the like. These preparations may also contain other therapeutically useful drugs.

While the content of the crystal of the present invention in these preparations varies depending on the dosage form, it can be generally contained at a concentration of 0.1-50 wt % in solid and semi-solid forms, and 0.05-10 wt % in liquid form.

While the dose of the crystal of the present invention varies widely according to the kind of warm-blooded animals including human to be the subject, the kind of the target disease, administration route, seriousness of symptoms, doctor's diagnosis and the like, it can be generally within the range of 0.01-5 mg/kg per day, preferably 0.02-2 mg/kg per day. It is obviously possible to administer a dose smaller than the above-mentioned lower limit or more than the above-mentioned upper limit, depending on seriousness of the symptom of patients, doctor's diagnosis and the like. The above-mentioned dose can be administered once a day or in several portions per day.

An example of a preparation containing Form I crystal of the present invention is shown below.

TABLE 1

| 5 mg tablet | mg/tablet |
| --- | --- |
| Form I crystal | 5.0 |
| starch | 10.0 |
| lactose | 73.0 |
| carboxymethylcellulose calcium | 10.0 |
| talc | 1.0 |
| magnesium stearate | 1.0 |
| | 100.0 |

Form I crystal is pulverized to a particle size 70 μm or less, starch, lactose and carboxymethylcellulose calcium are added thereto, and the mixture is mixed well. 10% Starch glue is added to the above-mentioned mixed powder, the mixture is mixed by stirring to produce granules. The granules are sieved to a particle size after drying of about 1000 μm, talc and magnesium stearate are admixed therewith, and the mixture is tableted.

EXAMPLES

The present invention is more specifically explained in the following by referring to Examples, which are not to be construed as limitative.

Production Example 1

Production of amorphous 2-(3,4-dichlorobenzyl)-5-methyl-4-oxo-3,4-dihydrothieno[2,3-d]pyrimidine-6-carboxylic acid A mixture of ethyl 2-(3,4-dichlorobenzyl)-5-methyl-4-oxo-3,4-dihydrothieno[2,3-d]pyrimidine-6-carboxylate (20.03 g), 5 mol/L aqueous sodium hydroxide solution (30 mL), water (50 mL) and isopropanol (30 mL) was heated under reflux for 1 hr. The reaction mixture was ice-cooled, acidified with dilute hydrochloric acid, and stirred for 2 hr under ice-cooling. The precipitated solid was collected by filtration, washed with water, and dried under reduced pressure at 80° C. for 24 hr to give a solid (17.39 g). The time necessary for collection by filtration was about 90 min.

By $^1$H-NMR and MS, the solid obtained in Production Example 1 was confirmed to be the same compound as 2-(3, 4-dichlorobenzyl)-5-methyl-4-oxo-3,4-dihydrothieno[2,3-d]pyrimidine-6-carboxylic acid described in Example 36-a) of patent document 1.

$^1$H-NMR (DMSO-d$_6$) δ: 2.79 (3H, s), 3.99 (2H, s), 7.3-7.7 (3H, m), 12.71 (1H, br s), 13.33 (1H, br s)

MS (m/z): 370 (M$^+$+2), 368 (M$^+$)

Example 1

Production of Form I crystal of 2-(3,4-dichlorobenzyl)-5-methyl-4-oxo-3,4-dihydrothieno[2,3-d]pyrimidine-6-carboxylic acid A mixture of amorphous 2-(3,4-dichlorobenzyl)-5-methyl-4-oxo-3,4-dihydrothieno[2,3-d]pyrimidine-6-carboxylic acid (4.995 g) obtained in Production Example 1, 1 mol/L aqueous sodium hydroxide solution (27.1 mL) and water (32 mL) was heated for 1 hr, and dissolution was confirmed. The reaction mixture was allowed to cool under room temperature, acidified with dilute hydrochloric acid, and stirred at 75° C. for 1.5 hr. The obtained crystals were collected by filtration, washed with water, and draught-dried at 40° C. for 19 hr to give the title crystal (4.835 g). The time necessary for collection by filtration was about 5 min.

By $^1$H-NMR and MS, the crystal obtained in Example 1 was confirmed to be the same compound as 2-(3,4-dichlorobenzyl)-5-methyl-4-oxo-3,4-dihydrothieno[2,3-d]pyrimidine-6-carboxylic acid described in Example 36-a) of patent document 1.

$^1$H-NMR (DMSO-d$_6$) δ: 2.79 (3H, s), 3.99 (2H, s), 7.3-7.7 (3H, m), 12.71 (1H, br s), 13.33 (1H, br s)

MS (m/z): 370 (M$^+$+2), 368 (M$^+$)

Figure 2:
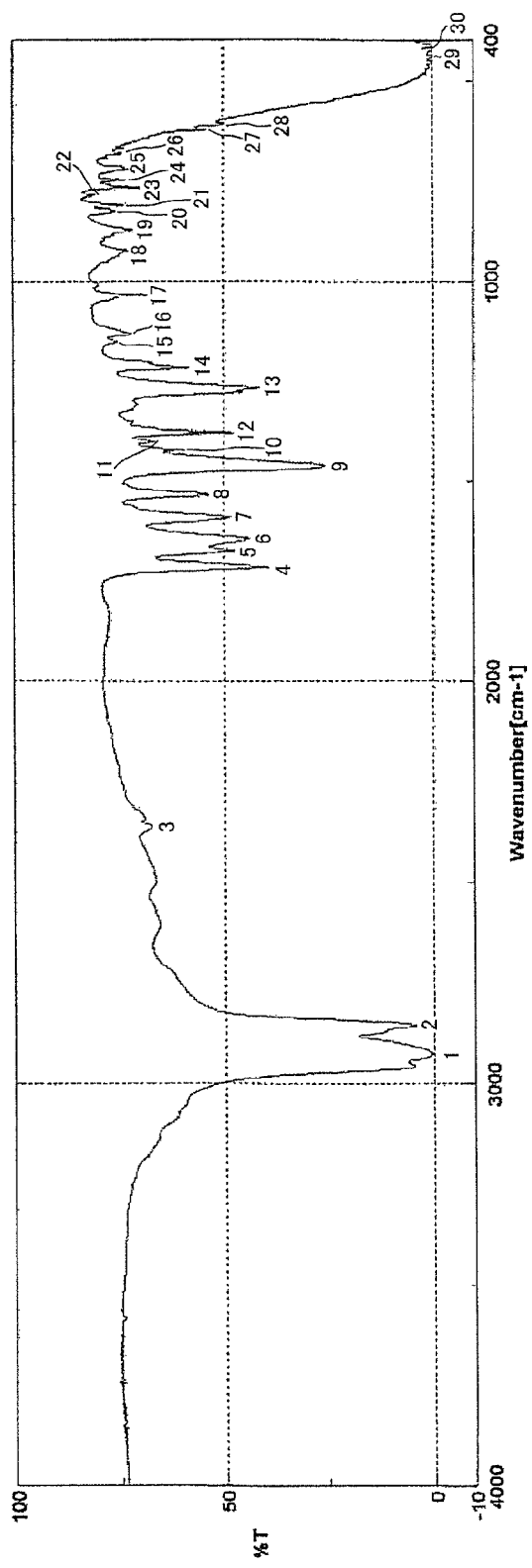
FIG. 2 shows an infrared absorption spectrum (paste method) of Form I crystal of compound A (Example 1).

The X-ray powder diffraction pattern of the crystal obtained in Example 1 is shown in FIG. 1, and the peaks and peak intensities at diffraction angle (2θ) are shown in Table 2. Furthermore, the infrared absorption spectrum is shown in FIG. 2.

TABLE 2

| Peak No. | 2 θ | Setting width for peak search | d value | Intensity | Relative intensity |
|---|---|---|---|---|---|
| 1 | 6.720 | 0.165 | 13.1426 | 52347 | 100 |
| 2 | 8.250 | 0.188 | 10.7084 | 15366 | 30 |
| 3 | 8.930 | 0.188 | 9.8944 | 17464 | 34 |
| 4 | 12.190 | 0.200 | 7.2547 | 8197 | 16 |
| 5 | 13.110 | 0.176 | 6.7476 | 9829 | 19 |
| 6 | 13.430 | 0.200 | 6.5875 | 10120 | 20 |
| 7 | 14.040 | 0.200 | 6.3026 | 27104 | 52 |
| 8 | 14.840 | 0.200 | 5.9646 | 33271 | 64 |
| 9 | 16.520 | 0.176 | 5.3616 | 7506 | 15 |
| 10 | 17.880 | 0.365 | 4.9568 | 11807 | 23 |
| 11 | 20.160 | 0.165 | 4.4010 | 6716 | 13 |
| 12 | 21.300 | 0.129 | 4.1680 | 6955 | 14 |
| 13 | 21.550 | 0.165 | 4.1202 | 10723 | 21 |
| 14 | 24.790 | 0.306 | 3.5885 | 8788 | 17 |
| 15 | 26.400 | 0.388 | 3.3732 | 48325 | 93 |
| 16 | 27.070 | 0.235 | 3.2912 | 8288 | 16 |
| 17 | 28.320 | 0.306 | 3.1488 | 8741 | 17 |
| 18 | 28.930 | 0.235 | 3.0837 | 6232 | 12 |

Example 2

Production of Form II crystal of 2-(3,4-dichlorobenzyl)-5-methyl-4-oxo-3,4-dihydrothieno[2,3-d]pyrimidine-6-carboxylic acid A mixture of amorphous 2-(3,4-dichlorobenzyl)-5-methyl-4-oxo-3,4-dihydrothieno[2,3-d]pyrimidine-6- carboxylic acid (5.671 g) obtained in Production Example 1, 1 mol/L aqueous sodium hydroxide solution (30.8 mL) and water (54 mL) was heated for 1 hr, and dissolution was confirmed. The reaction mixture was allowed to cool under room temperature, acidified with dilute hydrochloric acid, and stirred at 75° C. for 25 hr. The obtained crystals were collected by filtration, washed with water, and draught-dried at 40° C. for 19 hr to give the title compound (5.331 g). The time necessary for collection by filtration was about 5 min.

By $^1$H-NMR and MS, the crystal obtained in Example 2 was confirmed to be the same compound as 2-(3,4-dichlorobenzyl)-5-methyl-4-oxo-3,4-dihydrothieno[2,3-d]pyrimidine-6-carboxylic acid described in Example 36-a) of patent document 1.

$^1$H-NMR (DMSO-d$_6$) δ: 2.79 (3H, s), 3.99 (2H, s), 7.3-7.7 (3H, m), 12.71 (1H, br s), 13.33 (1H, br s)

MS (m/z): 370 (M$^+$+2), 368 (M$^+$)

Figure 3:
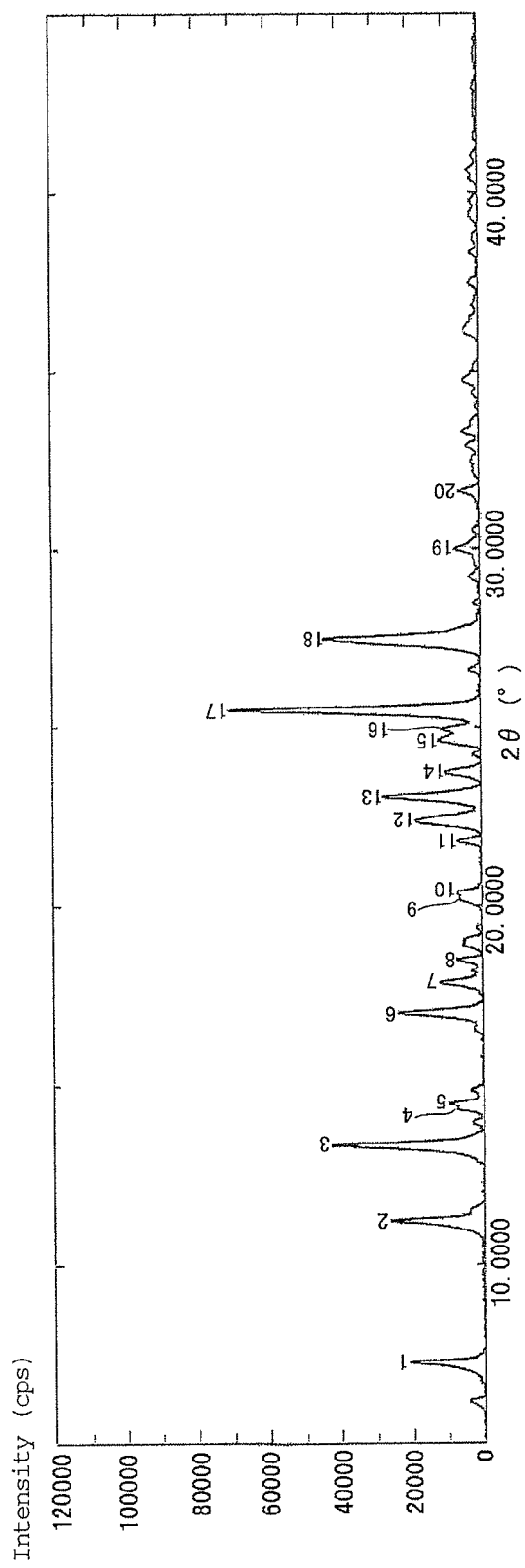
FIG. 3 shows an X-ray powder diffraction pattern of Form II crystal of compound A (Example 2).
Figure 4:
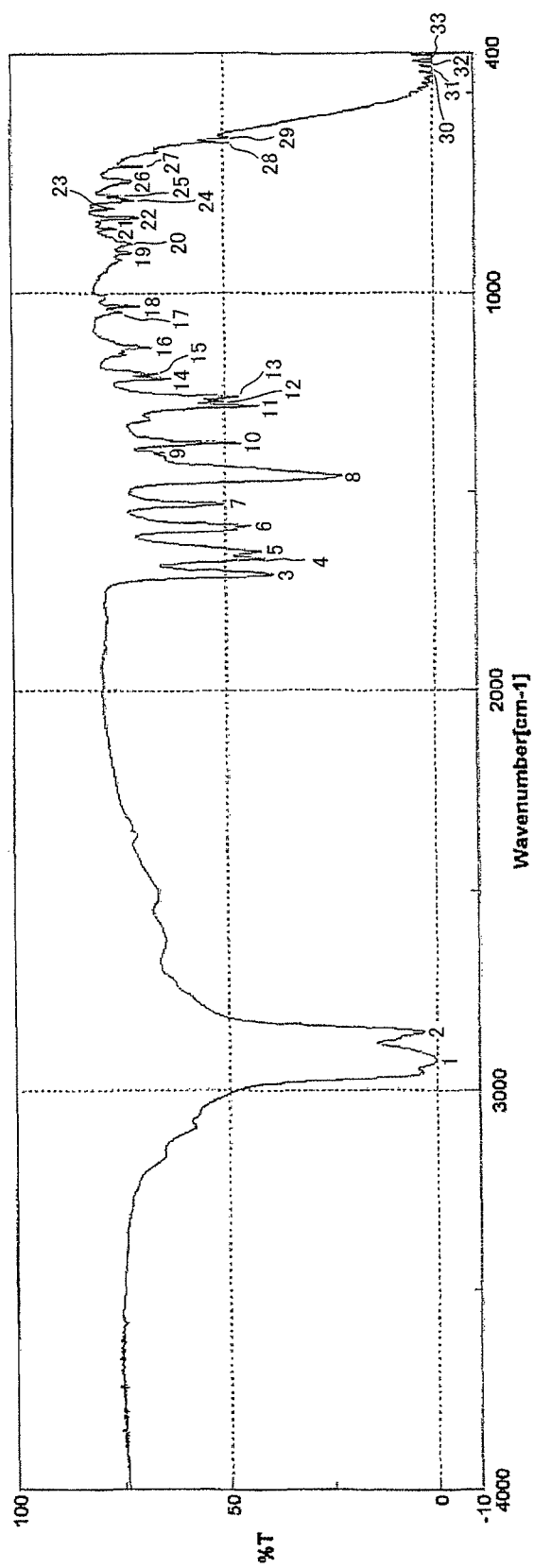
FIG. 4 shows an infrared absorption spectrum (paste method) of Form II crystal of compound A (Example 2).

The X-ray powder diffraction pattern of the crystal obtained in Example 2 is shown in FIG. 3, and the peaks and peak intensities at diffraction angle (2θ) are shown in Table 3. Furthermore, the infrared absorption spectrum is shown in FIG. 4.

TABLE 3

| Peak No. | 2 θ | Setting width for peak search | d value | Intensity | Relative intensity |
|---|---|---|---|---|---|
| 1 | 7.250 | 0.176 | 12.1830 | 18986 | 29 |
| 2 | 11.210 | 0.200 | 7.8866 | 24968 | 38 |
| 3 | 13.330 | 0.212 | 6.6367 | 40132 | 60 |
| 4 | 14.350 | 0.153 | 6.1672 | 6774 | 11 |
| 5 | 14.490 | 0.188 | 6.1079 | 8676 | 13 |
| 6 | 17.030 | 0.224 | 5.2022 | 22985 | 35 |
| 7 | 17.870 | 0.212 | 4.9595 | 11704 | 18 |
| 8 | 18.500 | 0.188 | 4.7920 | 6558 | 10 |
| 9 | 20.200 | 0.176 | 4.3924 | 5993 | 9 |
| 10 | 20.370 | 0.200 | 4.3561 | 6465 | 10 |
| 11 | 21.810 | 0.200 | 4.0717 | 6112 | 10 |
| 12 | 22.390 | 0.341 | 3.9675 | 18571 | 28 |
| 13 | 23.070 | 0.235 | 3.8521 | 26730 | 40 |
| 14 | 23.740 | 0.259 | 3.7448 | 9886 | 15 |
| 15 | 24.630 | 0.259 | 3.6115 | 11312 | 17 |
| 16 | 24.960 | 0.176 | 3.5645 | 10264 | 16 |
| 17 | 25.490 | 0.212 | 3.4916 | 67301 | 100 |
| 18 | 27.470 | 0.271 | 3.2442 | 42854 | 64 |
| 19 | 30.000 | 0.200 | 2.9761 | 6616 | 10 |
| 20 | 31.630 | 0.224 | 2.8264 | 5372 | 8 |

Reference Example 1

Production of crystal of isopropanol solvate of 2-(3, 4-dichlorobenzyl)-5-methyl-4-oxo-3,4-dihydrothieno [2,3-d]pyrimidine-6-carboxylic acid Amorphous 2-(3,4-dichlorobenzyl)-5-methyl-4-oxo-3,4-dihydrothieno[2,3-d]pyrimidine-6-carboxylic acid (1 g) obtained in Production Example 1 was suspended in isopropanol (25 mL), and the suspension was heated under reflux for 1 hr. After cooling to room temperature, the precipitate was collected by filtration, and draught-dried at 40° C. for 14 hr to give the title crystal (1.136 g).

$^1$H-NMR (DMSO-d$_6$) δ: 1.04 (6H, d, J=6.2 Hz), 2.79 (3H, s), 3.7-3.8 (1H, m), 3.99 (2H, s), 4.2-4.4 (1H, m), 7.3-7.7 (3H, m), 12.70 (1H, br s), 13.34 (1H, br s)

According to the above-mentioned NMR data, the obtained crystal is considered to be a mono isopropanol solvate of compound A.

Figure 5:
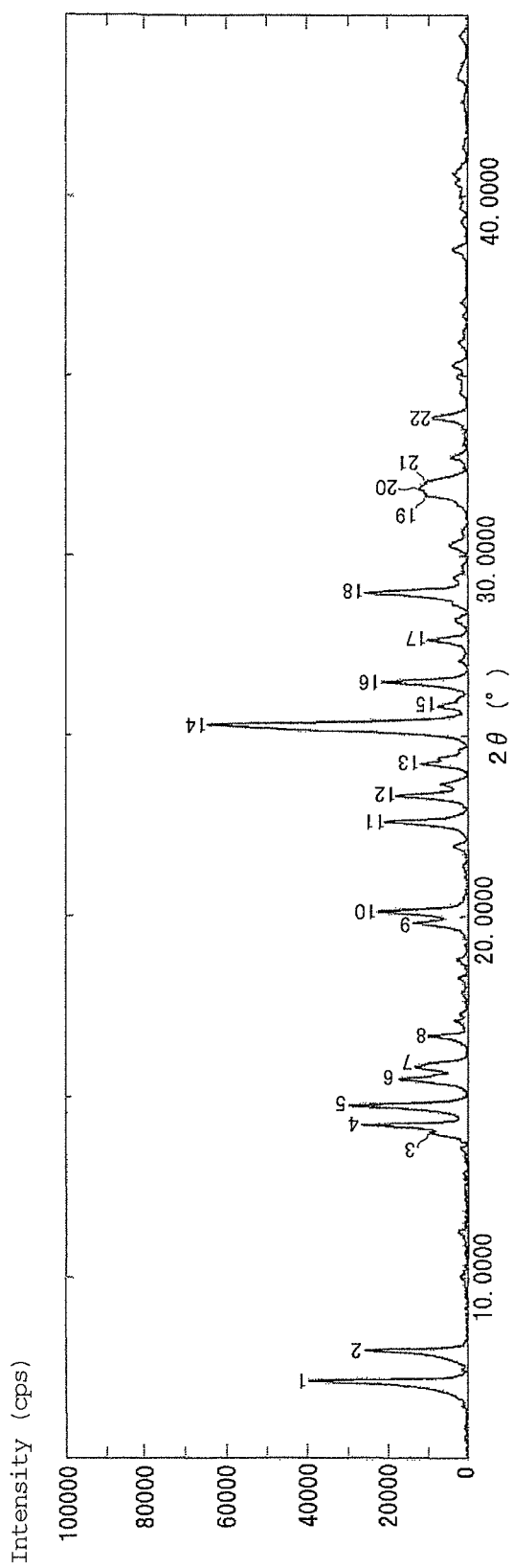
FIG. 5 shows an X-ray powder diffraction pattern of a crystal of an isopropanol solvate of compound A (Reference Example 1).
Figure 6:
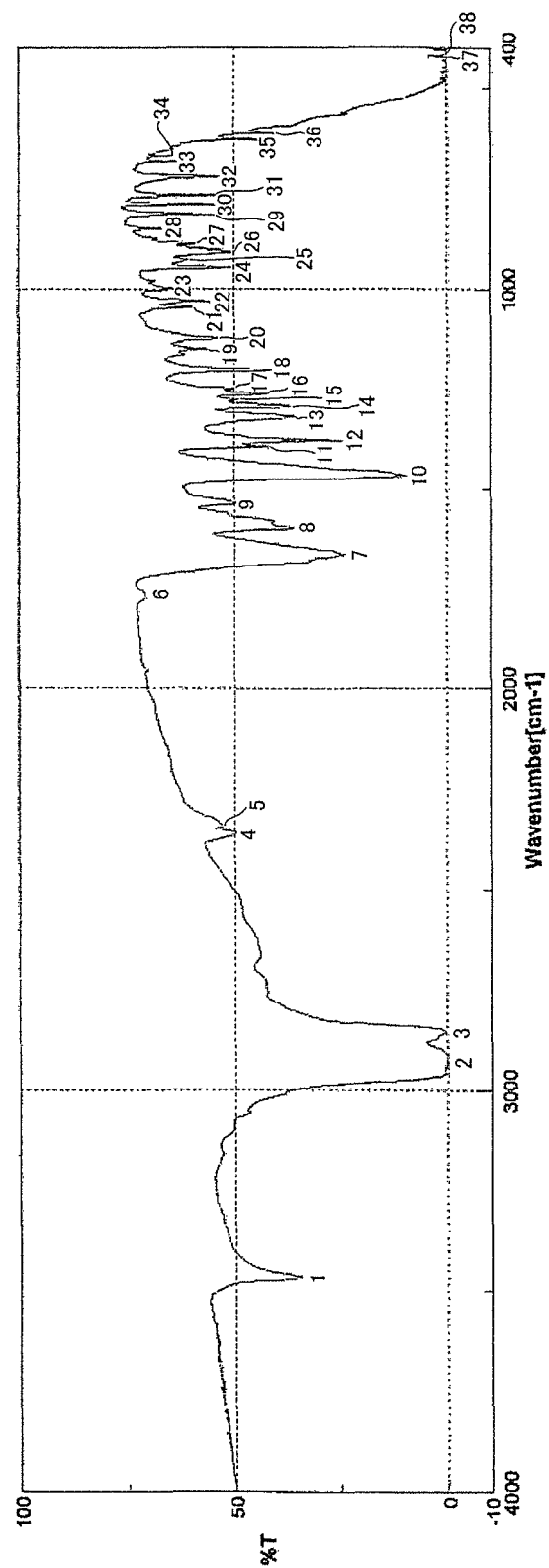
FIG. 6 shows an infrared absorption spectrum (paste method) of a crystal of an isopropanol solvate of compound A (Reference Example 1).

The X-ray powder diffraction patterns thereof are shown in FIG. 5, the peaks and peak intensities at diffraction angle (2θ) are shown in Table 4, and the infrared absorption spectrum is shown in FIG. 6.

TABLE 4

| Peak No. | 2 θ | Setting width for peak search | d value | Intensity | Relative intensity |
|---|---|---|---|---|---|
| 1 | 7.120 | 0.165 | 12.4051 | 33839 | 56 |
| 2 | 7.970 | 0.176 | 11.0839 | 21152 | 35 |
| 3 | 13.990 | 0.141 | 6.3250 | 8027 | 14 |
| 4 | 14.230 | 0.165 | 6.2189 | 22834 | 38 |
| 5 | 14.770 | 0.176 | 5.9927 | 26316 | 44 |
| 6 | 15.490 | 0.188 | 5.7158 | 15104 | 25 |
| 7 | 15.850 | 0.224 | 5.5867 | 12555 | 21 |
| 8 | 16.690 | 0.176 | 5.3074 | 8433 | 14 |
| 9 | 19.810 | 0.176 | 4.4780 | 11945 | 20 |
| 10 | 20.130 | 0.188 | 4.4075 | 20146 | 34 |
| 11 | 22.610 | 0.188 | 3.9294 | 18646 | 31 |
| 12 | 23.340 | 0.188 | 3.8081 | 16153 | 27 |
| 13 | 24.210 | 0.165 | 3.6732 | 9881 | 17 |
| 14 | 25.280 | 0.294 | 3.5201 | 60914 | 100 |
| 15 | 25.820 | 0.188 | 3.4477 | 6903 | 12 |
| 16 | 26.490 | 0.188 | 3.3620 | 18926 | 32 |
| 17 | 27.650 | 0.188 | 3.2235 | 8502 | 14 |
| 18 | 28.980 | 0.188 | 3.0785 | 23265 | 39 |
| 19 | 31.700 | 0.165 | 2.8203 | 10297 | 17 |
| 20 | 31.900 | 0.153 | 2.8031 | 11660 | 20 |
| 21 | 32.070 | 0.188 | 2.7886 | 9615 | 16 |
| 22 | 33.850 | 0.212 | 2.6459 | 8341 | 14 |

Reference Example 2

Production of crystal of dimethylacetamide solvate of 2-(3,4-dichlorobenzyl)-5-methyl-4-oxo-3,4-dihydrothieno[2,3-d]pyrimidine-6-carboxylic acid In the same manner as in Reference Example 1 except that dimethylacetamide (6 mL) and acetone (12 mL) were used instead of isopropanol, the title crystal was produced.

$^1$H-NMR (DMSO-$d_6$) δ: 1.96 (3H, s), 2.7-2.9 (6H, m), 2.95 (3H, s), 3.99 (2H, s), 7.3-7.7 (3H, m), 12.70 (1H, br s), 13.34 (1H, br s)

According to the above-mentioned NMR data, the obtained crystal is considered to be a mono dimethylacetamide solvate of compound A.

Figure 7:
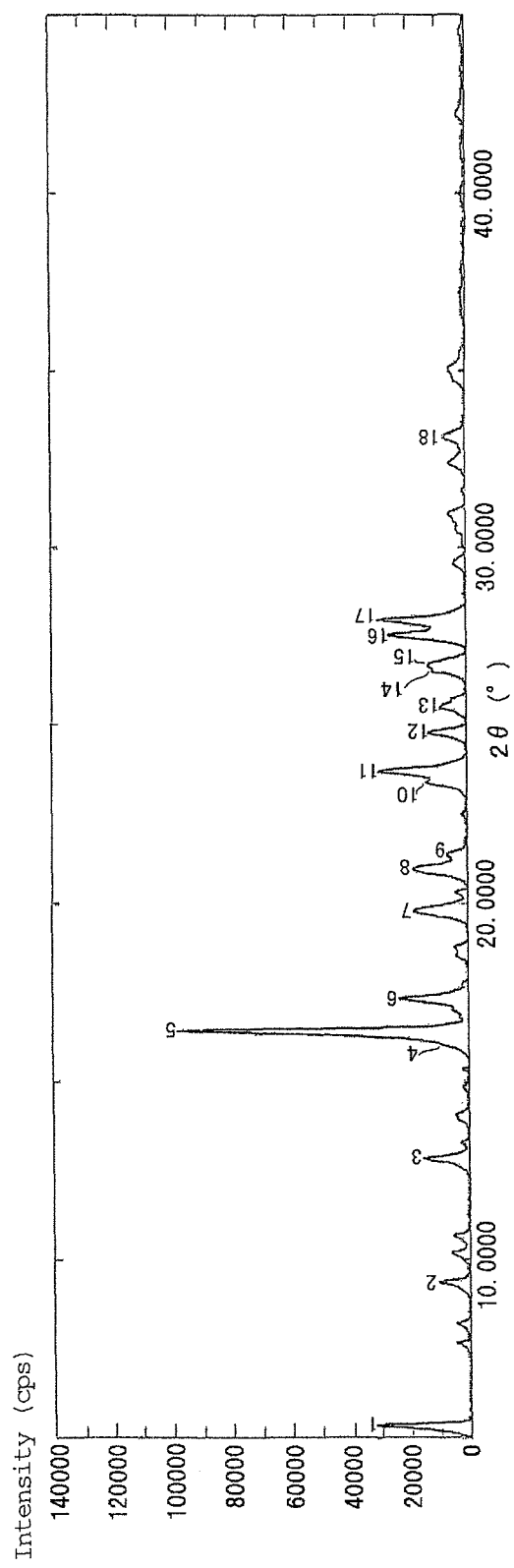
FIG. 7 shows an X-ray powder diffraction pattern of a crystal of a dimethylacetamide solvate of compound A (Reference Example 2).
Figure 8:
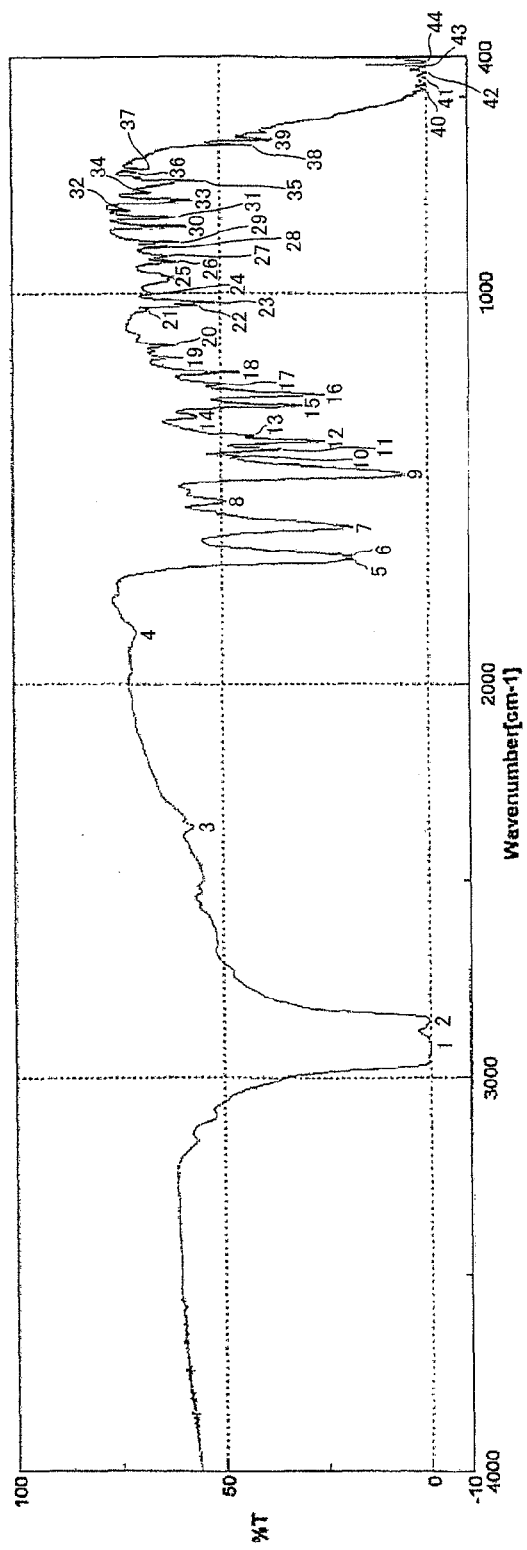
FIG. 8 shows an infrared absorption spectrum (paste method) of a crystal of a dimethylacetamide solvate of compound A (Reference Example 2).

The X-ray powder diffraction pattern is shown in FIG. 7, the peaks and peak intensities at diffraction angle (2θ) are shown in Table 5, and the infrared absorption spectrum is shown in FIG. 8.

TABLE 5

| Peak No. | 2 θ | Setting width for peak search | d value | Intensity | Relative intensity |
|---|---|---|---|---|---|
| 1 | 5.330 | 0.165 | 16.5665 | 28442 | 32 |
| 2 | 9.360 | 0.165 | 9.4408 | 9230 | 11 |
| 3 | 12.840 | 0.188 | 6.8888 | 14564 | 17 |
| 4 | 16.020 | 0.059 | 5.5278 | 7933 | 9 |
| 5 | 16.410 | 0.176 | 5.3973 | 89400 | 100 |
| 6 | 17.320 | 0.200 | 5.1157 | 22311 | 25 |
| 7 | 19.790 | 0.271 | 4.4825 | 18273 | 21 |
| 8 | 20.970 | 0.271 | 4.2328 | 18373 | 21 |
| 9 | 21.370 | 0.188 | 4.1545 | 6820 | 8 |
| 10 | 23.380 | 0.165 | 3.8017 | 13066 | 15 |
| 11 | 23.710 | 0.224 | 3.7495 | 28662 | 33 |
| 12 | 24.800 | 0.212 | 3.5871 | 12585 | 15 |
| 13 | 25.500 | 0.200 | 3.4902 | 8943 | 10 |
| 14 | 26.520 | 0.153 | 3.3582 | 11336 | 13 |
| 15 | 26.710 | 0.212 | 3.3348 | 12896 | 15 |
| 16 | 27.520 | 0.200 | 3.2384 | 25663 | 29 |
| 17 | 27.960 | 0.224 | 3.1885 | 29102 | 33 |
| 18 | 33.130 | 0.329 | 2.7018 | 7264 | 9 |

Reference Example 3

Production of crystal of dimethylformamide solvate of 2-(3,4-dichlorobenzyl)-5-methyl-4-oxo-3,4-dihydrothieno[2,3-d]pyrimidine-6-carboxylic acid Amorphous 2-(3,4-dichlorobenzyl)-5-methyl-4-oxo-3,4-dihydrothieno[2,3-d]pyrimidine-6-carboxylic acid (1 g) obtained Production Example 1 was dissolved in dimethylformamide (14 mL) and water (1 mL), and the mixture was left standing at room temperature for 24 hr. The precipitated crystals were collection by filtration, draught-dried at 40° C. for 14 hr to give the title crystal (904 mg).

$^1$H-NMR (DMSO-$d_6$) δ: 2.73 (3H, s), 2.79 (3H, s), 2.89 (3H, s), 3.99 (2H, s), 7.3-7.7 (3H, m), 7.95 (1H, s), 12.70 (1H, br s), 13.34 (1H, br s)

According to the above-mentioned NMR data, the obtained crystal is considered to be a mono dimethylformamide solvate of compound A.

Figure 9:
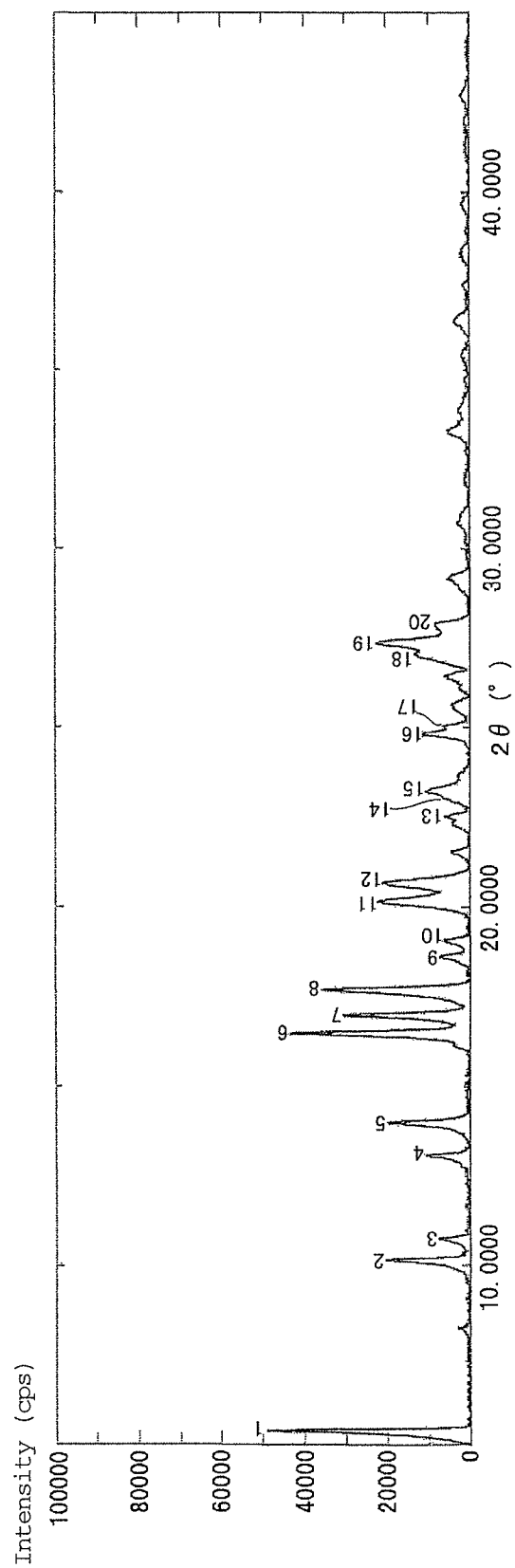
FIG. 9 shows an X-ray powder diffraction pattern of a crystal of a dimethylformamide solvate of compound A (Reference Example 3).
Figure 10:
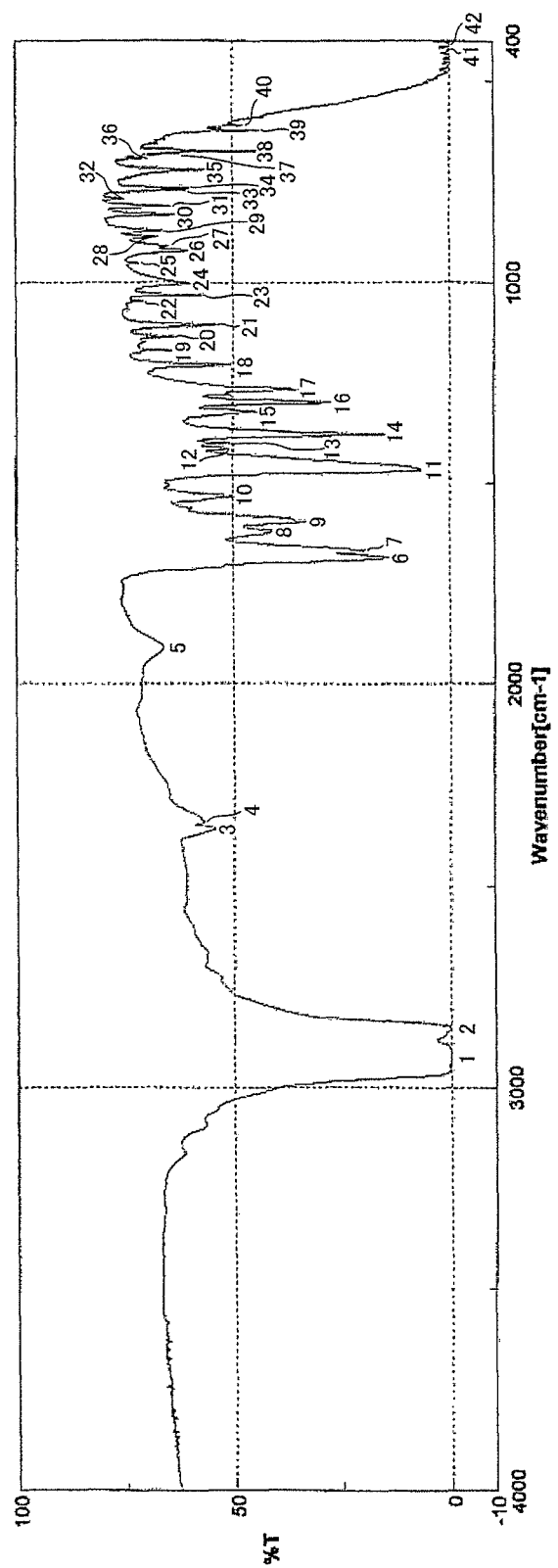
FIG. 10 shows an infrared absorption spectrum (paste method) of a dimethylformamide solvate of compound A (Reference Example 3).

The X-ray powder diffraction pattern is shown in FIG. 9, the peaks and peak intensities at diffraction angle (2θ) are shown in Table 6, and the infrared absorption spectrum is shown in FIG. 10.

TABLE 6

| Peak No. | 2 θ | Setting width for peak search | d value | Intensity | Relative intensity |
|---|---|---|---|---|---|
| 1 | 5.370 | 0.165 | 16.4432 | 39234 | 100 |
| 2 | 10.130 | 0.176 | 8.7249 | 17628 | 45 |
| 3 | 10.730 | 0.176 | 8.2383 | 6294 | 17 |
| 4 | 13.060 | 0.176 | 6.7733 | 9536 | 25 |
| 5 | 13.970 | 0.188 | 6.3341 | 17868 | 46 |
| 6 | 16.480 | 0.188 | 5.3746 | 38805 | 99 |
| 7 | 16.970 | 0.188 | 5.2205 | 27192 | 70 |
| 8 | 17.680 | 0.188 | 5.0124 | 32972 | 85 |
| 9 | 18.610 | 0.176 | 4.7639 | 6592 | 17 |
| 10 | 19.050 | 0.176 | 4.6549 | 5605 | 15 |
| 11 | 20.140 | 0.235 | 4.4054 | 22011 | 57 |
| 12 | 20.650 | 0.282 | 4.2977 | 20563 | 53 |
| 13 | 22.530 | 0.165 | 3.9431 | 5409 | 14 |
| 14 | 23.030 | 0.094 | 3.8587 | 5981 | 16 |
| 15 | 23.240 | 0.259 | 3.8243 | 10257 | 27 |
| 16 | 24.820 | 0.188 | 3.5843 | 10746 | 28 |
| 17 | 25.030 | 0.129 | 3.5547 | 5637 | 15 |
| 18 | 27.010 | 0.224 | 3.2984 | 12703 | 33 |
| 19 | 21.370 | 0.235 | 3.2558 | 22120 | 57 |
| 20 | 27.870 | 0.224 | 3.1986 | 8421 | 22 |

Reference Example 4

Production of crystal of 1,3-dimethyl-2-imidazolidinone solvate of 2-(3,4-dichlorobenzyl)-5-methyl-4-oxo-3,4-dihydrothieno[2,3-d]pyrimidine-6-carboxylic acid In the same manner as in Reference Example 3 except that 1,3-dimethyl-2-imidazolidinone was used as a solvent, the title crystal was produced.

$^1$H-NMR (DMSO-$d_6$) δ: 2.63 (12H, s), 2.79 (3H, s), 3.20 (8H, s), 3.99 (2H, s), 7.3-7.7 (3H, m), 12.70 (1H, br s), 13.34 (1H, br s)

According to the above-mentioned NMR data, the obtained crystal is considered to be a di 1,3-dimethyl-2-imidazolidinone solvate of compound A.

Figure 11:
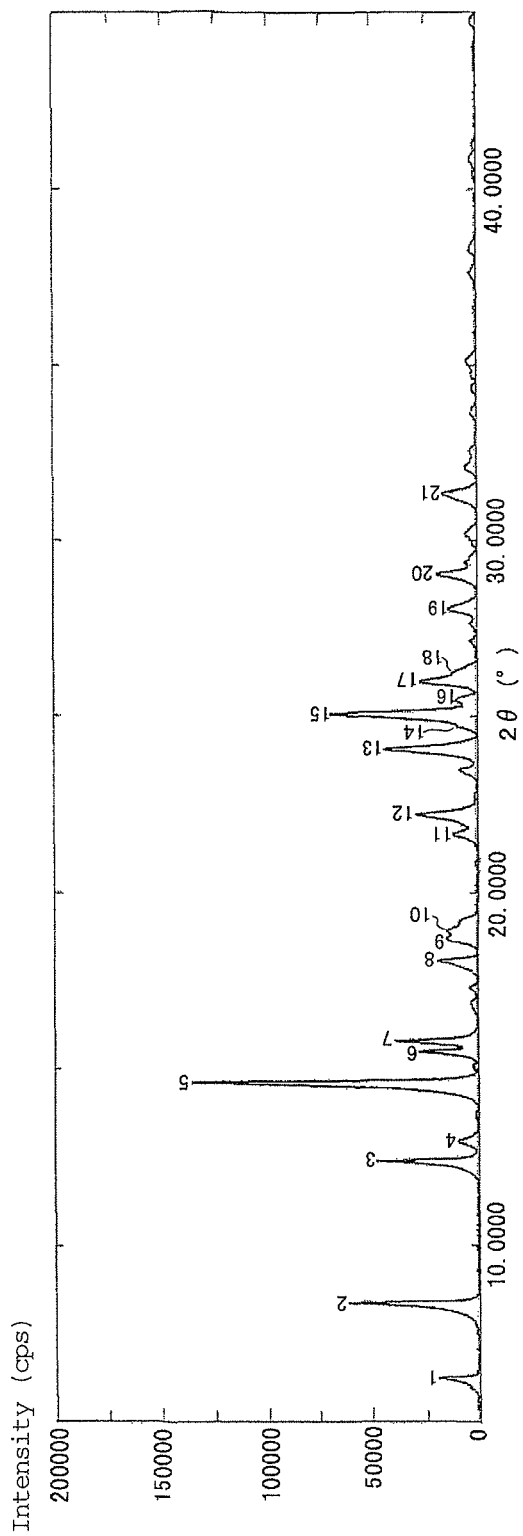
FIG. 11 shows an X-ray powder diffraction pattern of a crystal of a 1,3-dimethyl-2-imidazolidinone solvate of compound A (Reference Example 4).
Figure 12:
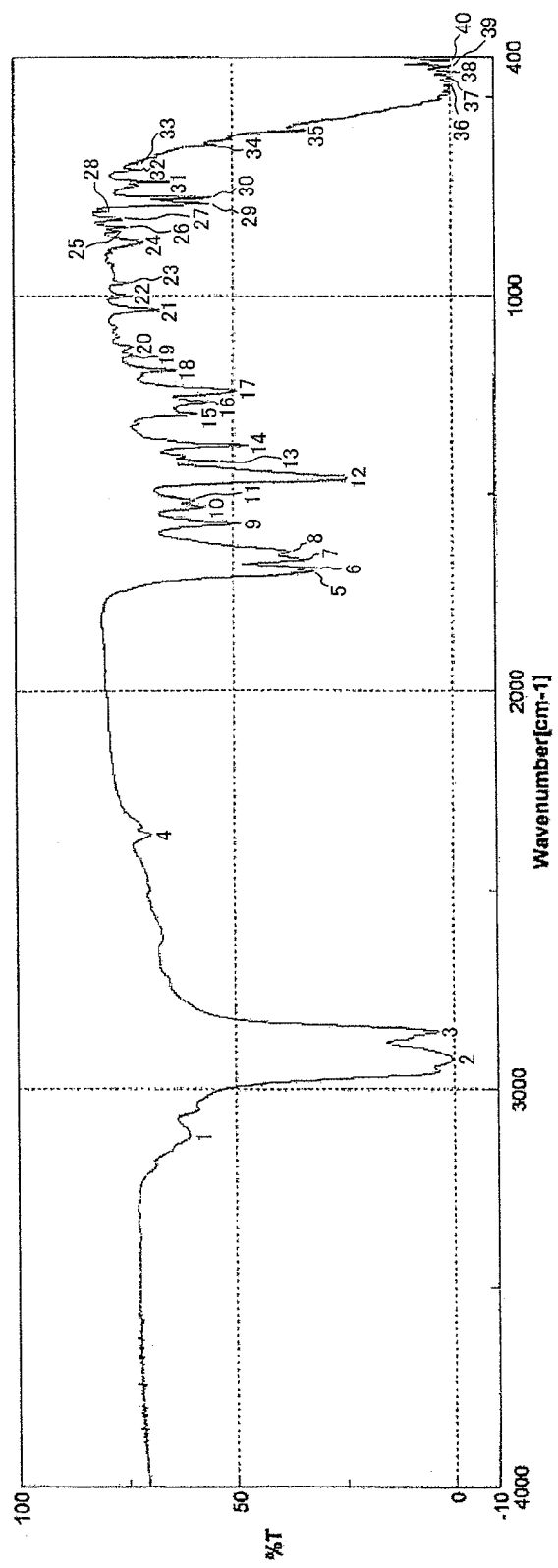
FIG. 12 shows an infrared absorption spectrum (paste method) of a crystal of a 1,3-dimethyl-2-imidazolidinone solvate of compound A (Reference Example 4).

The X-ray powder diffraction pattern is shown in FIG. 11, the peaks and peak intensities at diffraction angle (2θ) are shown in Table 7, and the infrared absorption spectrum is shown in FIG. 12.

TABLE 7

| Peak No. | 2 θ | Setting width for peak search | d value | Intensity | Relative intensity |
|---|---|---|---|---|---|
| 1 | 6.220 | 0.176 | 14.1979 | 15695 | 13 |
| 2 | 8.350 | 0.188 | 10.5803 | 52228 | 43 |
| 3 | 12.390 | 0.176 | 7.1380 | 41419 | 34 |
| 4 | 12.960 | 0.212 | 6.8253 | 8788 | 8 |
| 5 | 14.600 | 0.188 | 6.0621 | 121811 | 100 |
| 6 | 15.480 | 0.165 | 5.7194 | 23445 | 20 |
| 7 | 15.790 | 0.188 | 5.6078 | 33098 | 28 |
| 8 | 18.060 | 0.200 | 4.9078 | 16881 | 14 |
| 9 | 18.680 | 0.212 | 4.7462 | 14142 | 12 |
| 10 | 18.920 | 0.176 | 4.6866 | 14090 | 12 |
| 11 | 21.650 | 0.200 | 4.1014 | 10804 | 9 |
| 12 | 22.200 | 0.224 | 4.0010 | 28053 | 24 |
| 13 | 24.050 | 0.235 | 3.6973 | 41921 | 35 |
| 14 | 24.740 | 0.118 | 3.5957 | 9582 | 8 |
| 15 | 25.040 | 0.224 | 3.5533 | 65992 | 55 |
| 16 | 25.470 | 0.224 | 3.4943 | 9860 | 9 |
| 17 | 25.980 | 0.224 | 3.4268 | 26529 | 22 |
| 18 | 26.240 | 0.129 | 3.3934 | 11253 | 10 |
| 19 | 28.060 | 0.259 | 3.1773 | 13615 | 12 |
| 20 | 29.040 | 0.224 | 3.0723 | 18423 | 16 |
| 21 | 31.340 | 0.353 | 2.8519 | 16219 | 14 |

Reference Example 5

Production of crystal of N-methylpyrrolidone solvate of 2-(3,4-dichlorobenzyl)-5-methyl-4-oxo-3,4-dihydrothieno[2,3-d]pyrimidine-6-carboxylic acid In the same manner as in Reference Example 3 except that N-methylpyrrolidone was used as a solvent, the title crystal was produced.

$^1$H-NMR (DMSO-$d_6$) δ: 1.8-2.0 (3H, m), 2.1-2.3 (3H, m), 2.69 (4.5H, s), 2.79 (3H, s), 3.2-3.4 (3H, m), 3.99 (2H, s), 7.3-7.7 (3H, m), 12.70 (1H, br s), 13.34 (1H, br s)

According to the above-mentioned NMR data, the obtained crystal is considered to be a sesqui N-methylpyrrolidone solvate of compound A.

Figure 13:
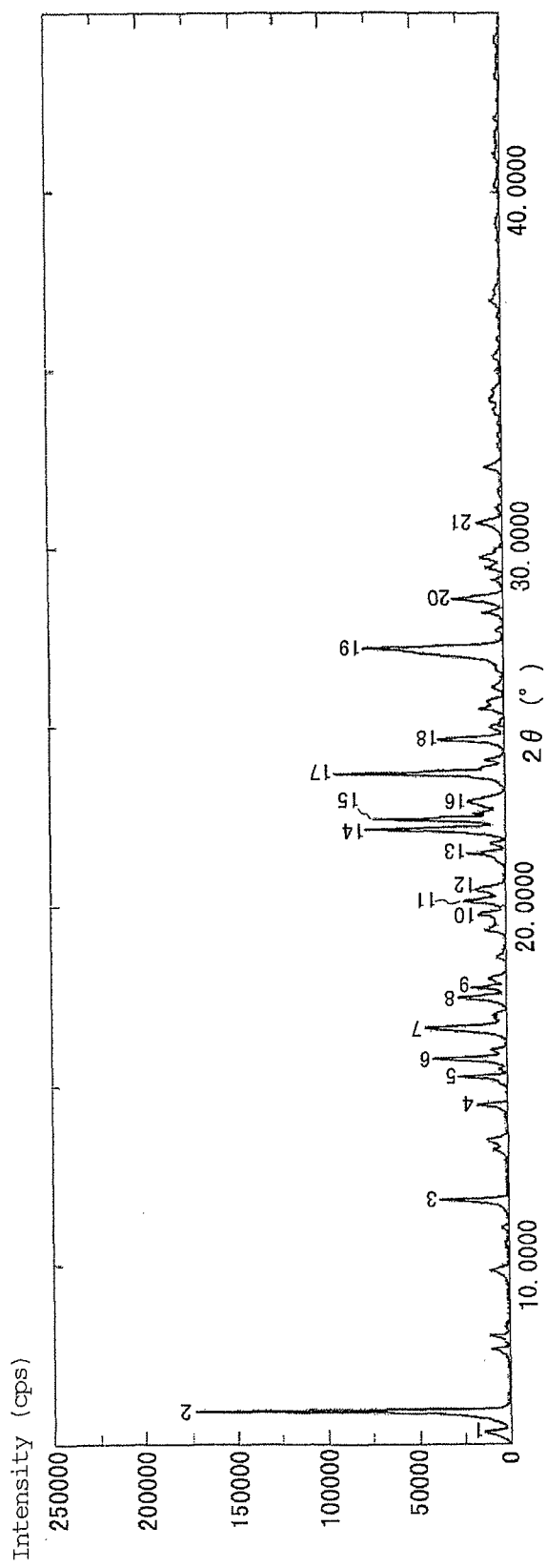
FIG. 13 shows an X-ray powder diffraction pattern of a crystal of an N-methylpyrrolidone solvate of compound A (Reference Example 5).
Figure 14:
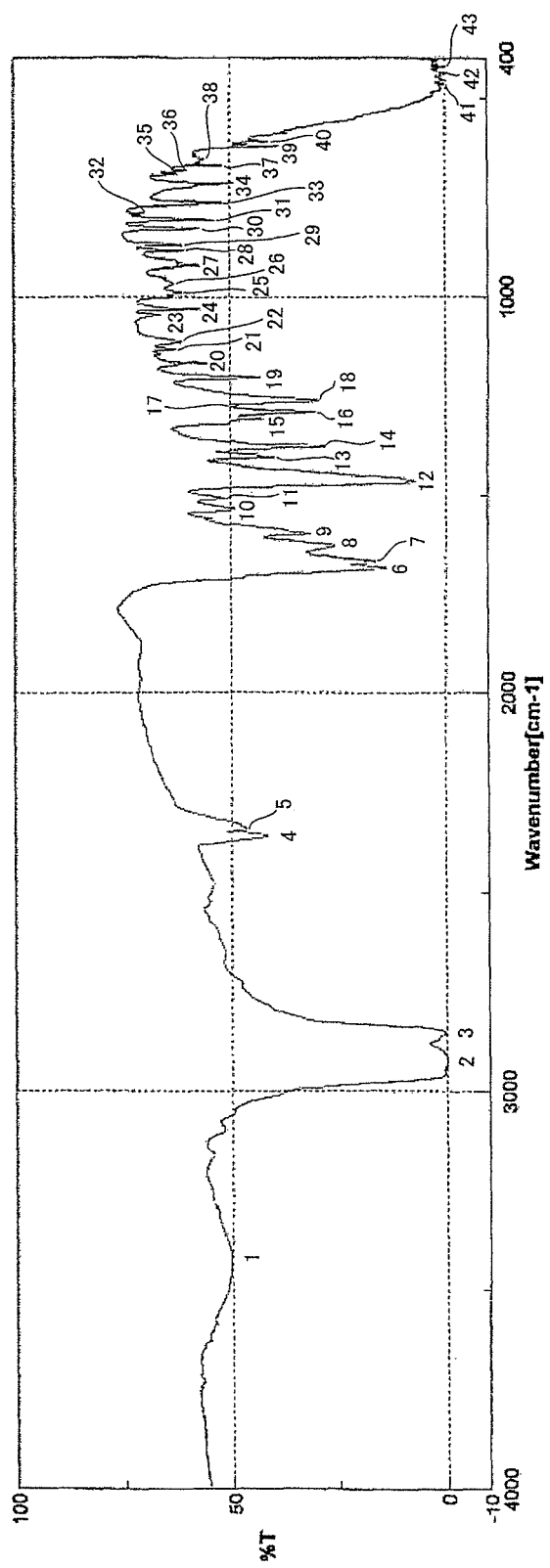
FIG. 14 shows an infrared absorption spectrum (paste method) of a crystal of an N-methylpyrrolidone solvate of compound A (Reference Example 5).

The X-ray powder diffraction pattern is shown in FIG. 13, the peaks and peak intensities at diffraction angle (2θ) are shown in Table 8, and the infrared absorption spectrum is shown in FIG. 14.

TABLE 8

| Peak No. | 2 θ | Setting width for peak search | d value | Intensity | Relative intensity |
|---|---|---|---|---|---|
| 1 | 5.320 | 0.188 | 16.5976 | 13478 | 13 |
| 2 | 5.920 | 0.176 | 14.9167 | 109648 | 100 |
| 3 | 11.800 | 0.165 | 7.4935 | 28799 | 97 |
| 4 | 14.460 | 0.176 | 6.1205 | 13122 | 12 |
| 5 | 15.240 | 0.165 | 5.8090 | 19620 | 18 |
| 6 | 15.750 | 0.165 | 5.6220 | 31601 | 29 |
| 7 | 16.600 | 0.188 | 5.3360 | 40775 | 38 |
| 8 | 17.450 | 0.176 | 5.0779 | 23183 | 22 |
| 9 | 17.730 | 0.153 | 4.9984 | 13302 | 13 |
| 10 | 19.780 | 0.165 | 4.4847 | 13353 | 13 |
| 11 | 20.150 | 0.176 | 4.4032 | 20094 | 19 |
| 12 | 20.460 | 0.212 | 4.3372 | 15586 | 15 |
| 13 | 21.470 | 0.165 | 4.1354 | 16776 | 15 |
| 14 | 22.140 | 0.176 | 4.0117 | 59636 | 55 |
| 15 | 22.420 | 0.153 | 3.9622 | 49753 | 46 |
| 16 | 22.930 | 0.259 | 3.8753 | 19478 | 18 |
| 17 | 23.700 | 0.176 | 3.7511 | 66432 | 61 |
| 18 | 24.650 | 0.176 | 3.6086 | 31269 | 29 |
| 19 | 27.190 | 0.212 | 3.2770 | 65626 | 60 |
| 20 | 28.570 | 0.200 | 3.1218 | 23291 | 22 |
| 21 | 30.720 | 0.200 | 2.9080 | 12884 | 12 |

The X-ray powder diffraction measurement of the crystal obtained in each Example was performed under the following conditions.

X-ray: CuKα/40 kV/40 mA
scan axis: 2θ/θ
scanning range: 5.0000-45.0000°
sampling width: 0.0100°
scan speed: 10.000° per minute The infrared absorption spectrum (paste method) measurement of the crystal obtained in each Example was performed under the following conditions. That is, liquid paraffin was added to a sample and kneaded well on an agate mortar, and infrared absorption spectrum was measured.

infrared absorption spectrum measuring apparatus: FT/IR-470 (JASCO Corporation)

$^1$H-NMR was measured using JNM-ECP400 (JEOL Ltd.) in DMSO-$d_6$ at 400 Mz.

Example 3

Consideration of maturation temperature and maturation time of aqueous suspension 2-(3,4-dichlorobenzyl)-5-methyl-4-oxo-3,4-dihydrothieno[2,3-d]pyrimidine-6-carboxylic acid A mixture of 2-(3,4-dichlorobenzyl)-5-methyl-4-oxo-3,4-dihydrothieno[2,3-d]pyrimidine-6-carboxylic acid mono sodium salt (4.992 g) produced from amorphous 2-(3,4-dichlorobenzyl)-5-methyl-4-oxo-3,4-dihydrothieno[2,3-d]pyrimidine-6-carboxylic acid produced by the method described in Production Example 1 and sodium hydroxide by a conventional method, 1 mol/L aqueous sodium hydroxide solution (12.8 mL) and water (45 mL) was heated, and dissolution was confirmed. The reaction mixture was allowed to cool under room temperature, acidified with dilute hydrochloric acid and matured at the temperature described in Table 9. The precipitated crystals were sampled over time, and production and disappearance of Form I crystal and Form II crystal was measured by X-ray powder diffraction. To be specific, as for Form I crystal, appearance and disappearance of characteristic X-ray powder diffraction peaks 2θ of about 14.8° and about 26.4° were analyzed, and as for Form II crystal, appearance of characteristic X-ray powder diffraction peaks 2θ of about 11.2° and about 25.5° was analyzed. The results are shown in Table 9.

TABLE 9

| temperature (° C.) | observation of Form I crystal alone | appearance of Form II crystal (mixture of Form I and Form II) | observation of Form II crystal alone |
|---|---|---|---|
| 45 | 1 h, 72 h, 96 h | 312 h | 408 h |
| 55 | 0.5 h, 24 h, 32 h | 48 h, 168 h | 192 h |
| 65 | 0.5 h, 24 h | 120 h | 144 h |
| 75 | 0.1 h, 12 h | | 25 h |
| 85 | 0.05 h, 5 h, 6 h | 15 h, 22 h | 23 h |
| 95 | 0.01 h, 4 h | 5 h, 10 h | 16 h |

Experimental Example 1

Thermal Stability

Form I crystal obtained in Example 1 and Form II crystal obtained in Example 2 and amorphous compound A obtained in Production Example 1 were heated at 100° C. for 6 hr or 200° C. for 6 hr, and the amount of the decomposition product 2-(3,4-dichlorobenzyl)-5-methyl-4-oxo-3,4-dihydrothieno[2,3-d]pyrimidine (decarboxylation substance of compound A) was measured by HPLC. The results thereof and the color of each sample then are shown in the following Table 10. In the HPLC measurement, the sample was suspended in a mobile phase, dissolved by adding 1 equivalent of aqueous sodium hydroxide and then applied.

HPLC Measurement Condition
  measuring apparatus: Waters Alliance HPLC system
  detector: ultraviolet absorption spectrophotometer (measurement wavelength 225 nm)
  column: XBridge C18 (Waters)
  column temperature: constant temperature near 30° C.
  mobile phase A: acetonitrile
  mobile phase B: 5 mmol/L ammonium hydrogen carbonate (pH 8.0) gradient method of mobile phase A and mobile phase B: mobile phase A 23% (0 to 15 min), mobile phase A 23%→55% (15 to 30 min), mobile phase A 55% (30 to 50 min)
  flow rate: 1.0 mL/min

TABLE 10

| temperature and time | Form I crystal | Form II crystal | Amorphous form |
|---|---|---|---|
| 100° C., 6 hr | 0%, white | 0%, white | 0.006%, slight brown |
| 200° C., 6 hr | 0.05%, slight brown | 0.07%, slight brown | 3.42%, pale-brown |

Experimental Example 2

Solubility

Form I crystal obtained in Example 1, Form II crystal obtained in Example 2 and amorphous compound A obtained in Production Example 1 (each 50 mg) were suspended in 0.5% aqueous Tween80 solution (20 mL), sonicated, aqueous 0.5% Tween80 solution (180 mL) was added and the mixture was stirred at 37° C.

The solubility was measured by HPLC under the same conditions (isocratic method using acetonitrile/5 mmol/L ammonium hydrogen carbonate (pH 8.0) (27:73) for mobile phase) as in Experimental Example 1 at the time points of 0.5 hr, 1 hr, 2 hr, 3 hr, 4 hr, 5 hr, and 6 hr from the start of stirring. As a result, amorphous compound A reached near saturation at about 0.5 hr, Form I crystal reached near saturation at about 1 hr and Form II crystal reached near saturation at about 2 hr. Therefore, the value of 3 hr was taken as the solubility. The results are shown in Table 11 below together with the results of the following Experimental Example 3.

Experimental Example 3

Dissolution Rate

Form I crystal obtained in Example 1, Form II crystal obtained in Example 2 and amorphous compound A obtained in Production Example 1 (each 100 mg) were compression molded by a tableting machine for IR measurement having a metal mold pre-treated with magnesium stearate, and formed into discs (diameter 12 mm). Each disc was added to 0.5% aqueous Tween80 solution (900 mL, 37° C.), the concentration was measured every 10 minutes up to 1 hr, and every 1 hour after 1 hr up to 3 hr, by HPLC under the same conditions as in Experimental Example 1 (isocratic method using acetonitrile/5 mmol/L ammonium hydrogen carbonate (pH 8.0) (27:73) for mobile phase) while maintaining the temperature at 37° C. according to the dissolution test apparatus Paddle Method (50 rpm), and each dissolution rate was calculated. The results are shown in Table 11 below together with the results of the above-mentioned Experimental Example 2.

TABLE 11

|  | Form I crystal | Form II crystal | Amorphous form |
|---|---|---|---|
| solubility (µg/mL) | 15 | 10 | 37 |
| dissolution rate (µg/mL/min) | 0.0017 | 0.0011 | 0.0052 |

From the results of Experimental Examples 1 to 3, it is clear that Form I crystal is superior to Form II crystal in the thermal stability, and higher in the solubility and dissolution rate than Form II crystal. The results show that Form I crystal is more superior when used as, for example, a pharmaceutically active ingredient of oral administration preparations such as tablet and the like, an adhesive preparation and the like. On the other hand, when used as a pharmaceutically active ingredient of a sustained-release preparation, Form II crystal is useful since its concentration does not become high, which leads to the reduction of side effects.

Experimental Example 4

Thermoanalysis

Figure 15:
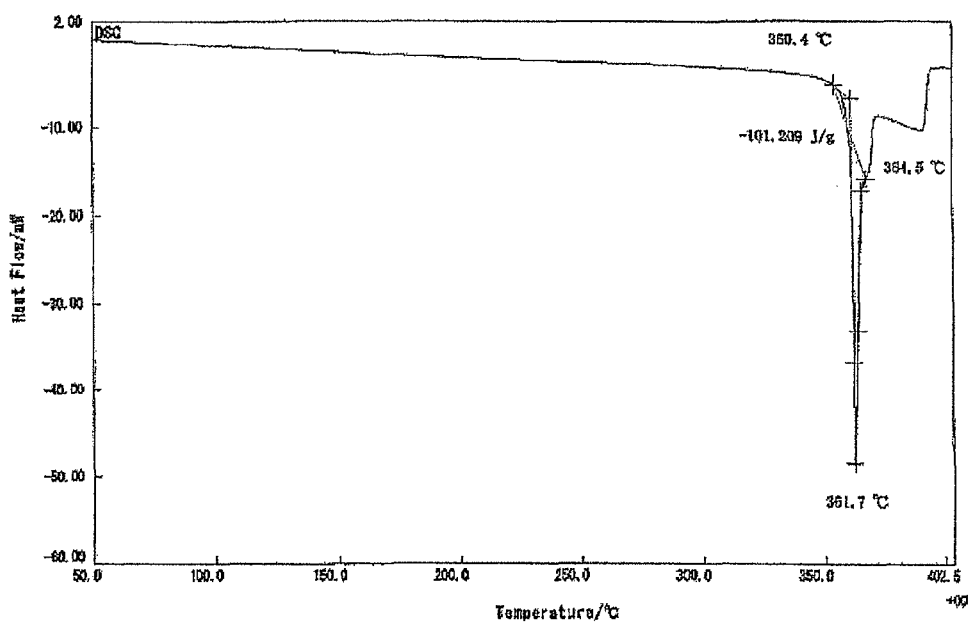
FIG. 15 shows a DSC chart of Form I crystal of compound A (Example 1).
Figure 16:
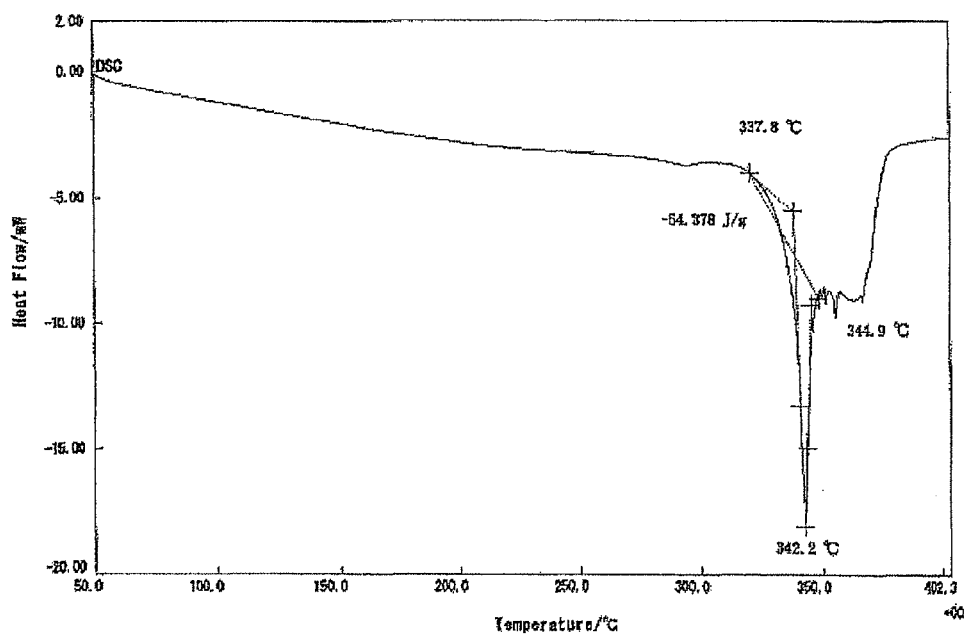
FIG. 16 shows a DSC chart of Form II crystal of compound A (Example 2).

Form I crystal obtained in Example 1 and Form II crystal obtained in Example 2 were subjected to the measurement of differential scanning calorimetry (DSC) using aluminum oxide as a control. The measurement conditions are as follows.
  sample container: open
  heating temperature: 10.0° C./min up to 400° C.
  measurement temperature range: 50 to 400° C.
  atmospheric gas: nitrogen gas
The DSC chart of each crystal is shown in FIG. 15 and FIG. 16.

Experimental Example 5

Comparison of Filtration Speed

Form I crystal, Form II crystal and amorphous compound A were subjected to the measurement of the speed of filtration from a water suspension. In the test, the same synthesis scale, the same solvent amount, the same filtration apparatus (glass filter) and the same level of reduced pressure were used for comparison. Experimental Examples are shown in the following and the results thereof are shown in Table 12 below.

Experimental Example 5-a

Filtration speed of amorphous 2-(3,4-dichlorobenzyl)-5-methyl-4-oxo-3,4-dihydrothieno[2,3-d]pyrimidine-6-carboxylic acid A mixture of 2-(3,4-dichlorobenzyl)-5-methyl-4-oxo-3,4-dihydrothieno[2,3-d]pyrimidine-6-carboxylic acid mono sodium salt (2.501 g), 1 mol/L aqueous sodium hydroxide solution (9.6 mL) and water (39.4 mL) was dissolved by stirring. The reaction mixture was ice-cooled, ethanol (10 mL) was added, the inside temperature was set to about 2° C., neutralized with 1 mol/L hydrochloric acid (16.0 mL), water (25.0 mL) was added (solvent amount was set to 100 mL), and the mixture was stirred under ice-cooling to confirm that the inside temperature was about 1° C. The suspension was poured into a G2 glass filter (diameter 3 cm), and the pressure reduction was started at 50 hpa. The time necessary to the increase of pressure by the completion of filtration was 42 minutes 52 seconds. The height of the solid at that time was 4.3 cm (bulk 30.4 cm$^3$). Washing with water was not possible due to clogging.

Experimental Example 5-b

Filtration speed of Form I crystal of 2-(3,4-dichlorobenzyl)-5-methyl-4-oxo-3,4-dihydrothieno[2,3-d]pyrimidine-6-carboxylic acid A mixture of 2-(3,4-dichlorobenzyl)-5-methyl-4-oxo-3,4-dihydrothieno[2,3-d]pyrimidine-6-carboxylic acid mono sodium salt (2.502 g), 1 mol/L aqueous sodium hydroxide solution (6.4 mL) and water (22.5 mL) was dissolved by stirring with heating. The reaction mixture was allowed to cool under room temperature, neutralized with 1 mol/L hydrochloric acid (12.8 mL), and water (8.3 mL) was added. The mixture was stirred at about 75° C. for 1.5 hr, water (50 mL) was added (solvent amount was set to 100 mL), and the mixture was cooled to about 21° C. The suspension was poured into a G2 glass filter (diameter 3 cm), and the pressure reduction was started at 50 hpa. The time necessary to the increase of pressure by the completion of filtration was 4 minutes 14 seconds. The height of the solid at that time was 2.3 cm (bulk 16.2 cm$^3$). Then, an operation of washing the obtained solid with water (25 mL), followed by reduced pressure filtration at 50 hpa was repeated 3 times to confirm that the filtrate had pH 7. At this point, the total filtration time necessary for increasing the pressure was 10 minutes 2 seconds and the height of the final solid was 1.5 cm (bulk 10.6 cm$^3$).

Experimental Example 5-c

Filtration speed of Form II crystal of 2-(3,4-dichlorobenzyl)-5-methyl-4-oxo-3,4-dihydrothieno[2,3-d]pyrimidine-6-carboxylic acid A mixture of 2-(3,4-dichlorobenzyl)-5-methyl-4-oxo-3,4-dihydrothieno[2,3-d]pyrimidine-6-carboxylic acid mono sodium salt (2.503 g), 1 mol/L aqueous sodium hydroxide solution (6.4 mL) and water (22.5 mL) was dissolved by stirring with heating. The reaction mixture was allowed to cool under room temperature, neutralized with 1 mol/L hydrochloric acid (12.8 mL), and water (8.3 mL) was added. The mixture was stirred with heating under reflux for 8 hr, and further at about 70° C. for 8 hr. Water (50 mL) was added (solvent amount was set to 100 mL), and the mixture was cooled to about 21° C. The suspension was poured into a G2 glass filter (diameter 3 cm), and the pressure reduction was started at 50 hpa. The time necessary to the increase of pressure by the completion of filtration was 4 minutes 5 seconds. The height of the solid at that time was 2.1 cm (bulk 14.8 cm$^3$). Then, an operation of washing the obtained solid with water (25 mL), followed by reduced pressure filtration at 50 hpa was repeated 3 times to confirm that the filtrate had pH 7. At this point, the total filtration time necessary for increasing the pressure was 6 minutes 33 seconds and the height of the final solid was 1.6 cm (bulk 11.3 cm$^3$).

TABLE 12

| form | filtration operation time | bulk after filtration operation | time of washing with water (25 mL × 3, washed until pH 7) | bulk after washing with water | note |
|---|---|---|---|---|---|
| amorphous | 42 min 52 sec | 30.4 cm$^3$ | washing impossible due to clogging | — | amorphous form turned into a gel by water absorption, and solid-liquid separation was difficult |
| Form I | 4 min 14 sec | 16.2 cm$^3$ | 10 min 2 sec | 10.6 cm$^3$ | |
| Form II | 4 min 5 sec | 14.8 cm$^3$ | 6 min 33 sec | 11.3 cm$^3$ | |

Experimental Example 6

Dog Absorption Test

Form I crystal, Form II crystal and amorphous form of compound A were subjected to a dog absorption test under the following conditions. The results are shown in Table 13. Form I crystal, Form II crystal and amorphous form of compound A showed good pharmacokinetics as a medicament.

sample: except for amorphous form, samples of Form I crystal and Form II crystal sieved to have a particle size of 20 to 63 μm by wet classification (two kinds of sieves and flowing water were used) were used.

Preparation method: 25 mL of water was added to a sample (3 g), and the mixture was gently pulverized in a mortar, classified under pressurization, and draught-dried. As amorphous form, a sample pulverized in agate mortar was used.

method: 9 dogs, 3×3 crossover, 0.3 mg/kg oral administration

TABLE 13

| Parameters | units | Form I average | Form II average | amorphous average |
|---|---|---|---|---|
| $T_{1/2}$ | hr | 3.50 | 3.32 | 3.05 |
| Tmax | hr | 3.06 | 3.44 | 3.78 |
| Cmax | ng/mL | 9.1 | 3.7 | 10.3 |
| $AUC_{0-t}$ | ng·hr/mL | 64.6 | 24.2 | 62.9 |
| $AUC_{inf}$ | ng·hr/mL | 65.6 | 24.2 | 63.4 |
| MRT | hr | 6.73 | 6.89 | 6.31 |

Experimental Example 7

Photostability Test

Figure 17:
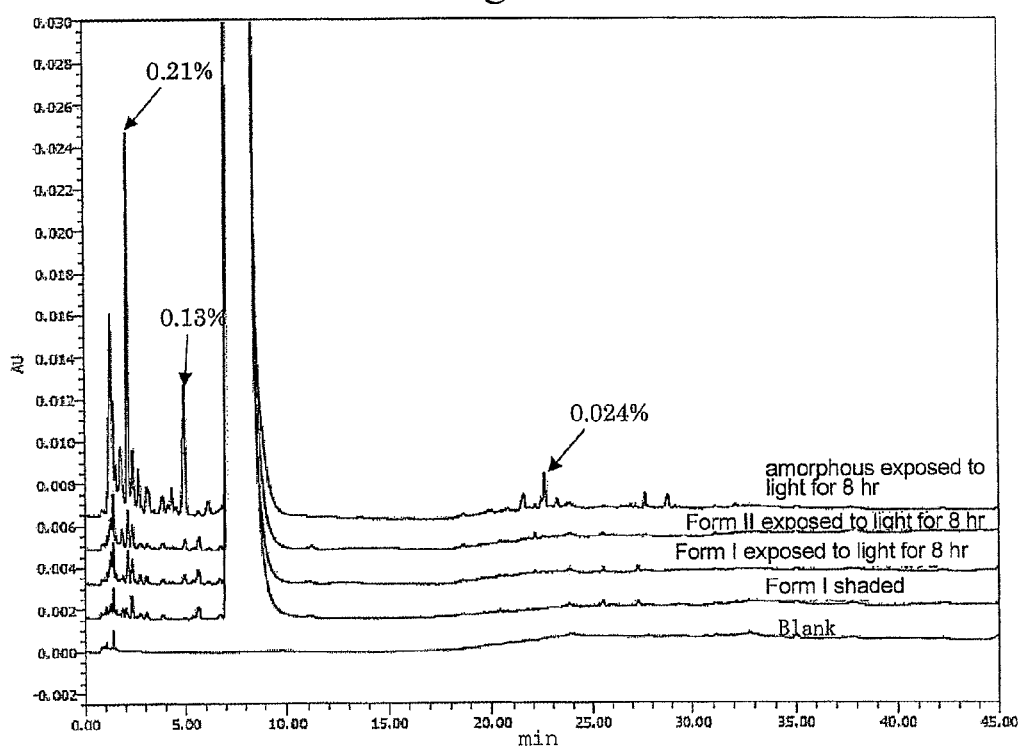
FIG. 17 shows an HPLC chart showing the photostability of compound A (Experimental Example 7).

Form I crystal, Form II crystal and amorphous form of compound A were subjected to a photostability test under the following conditions. The results are shown in FIG. 17. light source: xenon lamp 18 million Lxs conditions: sample (6 mg) was weighed in a transparent sample bottle, and exposed to light for 8 hr.

HPLC conditions: same as in Experimental Example 1

Form I and Form II crystals were comparatively stable, but the amorphous form contained impurity exceeding 0.2%.

INDUSTRIAL APPLICABILITY

The crystal of the present invention is suitable as an active ingredient of a medicament for the treatment, procedure and the like of dysuria and the like, since it can be produced by a convenient method suitable for industrial large-scale production, and is stable.

This application is based on patent application No. 2010-125362 filed in Japan, the contents of which are encompassed in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A crystal of 2-(3,4-dichlorobenzyl)-5-methyl-4-oxo-3,4-dihydrothieno[2,3-d]pyrimidine-6-carboxylic acid, having an X-ray powder diffraction pattern showing diffraction peaks at diffraction angles 2θ of 7.3±0.2°, 11.2±0.2°, 13.3±0.2°, 17.0±0.2°, 25.5±0.2° and 27.5±0.2° in X-ray powder diffraction spectrum.

2. The crystal according to claim 1, which is an unsolvated and unhydrated crystal.

3. The crystal according to claim 1, showing an endothermic peak having a peak top temperature of 342±5° C. in differential scanning calorimetry.

4. The crystal according to claim 3, which is an unsolvated and unhydrated crystal.

5. A pharmaceutical composition comprising the crystal according to claim 1 and a pharmaceutically acceptable carrier.

6. A pharmaceutical composition comprising the crystal according to claim 2 and a pharmaceutically acceptable carrier.

7. A pharmaceutical composition comprising the crystal according to claim 3 and a pharmaceutically acceptable carrier.

8. A pharmaceutical composition comprising the crystal according to claim 4 and a pharmaceutically acceptable carrier.

9. A method of modulating phosphodiesterase-9 activity in a mammal, which comprises administering an effective amount of the crystal according to claim 1 to a mammal in need thereof.

10. A method of modulating phosphodiesterase-9 activity in a mammal, which comprises administering an effective amount of the crystal according to claim 2 to a mammal in need thereof.

11. A method of modulating phosphodiesterase-9 activity in a mammal, which comprises administering an effective amount of the crystal according to claim 3 to a mammal in need thereof.

12. A method of modulating phosphodiesterase-9 activity in a mammal, which comprises administering an effective amount of the crystal according to claim 4 to a mammal in need thereof.

13. A method of producing the crystal according to claim 1, comprising heating an aqueous suspension of 2-(3,4-dichlorobenzyl)-5-methyl-4-oxo-3,4-dihydrothieno[2,3-d]pyrimidine-6-carboxylic acid.

14. A method of producing the crystal according to claim 1, comprising heating an aqueous suspension of 2-(3,4-dichlorobenzyl)-5-methyl-4-oxo-3,4-dihydrothieno[2,3-d]pyrimidine-6-carboxylic acid at not less than 60° C. and less than 70° C. for 144 hr or more, not less than 70° C. and less than 80° C. for 25 hr or more, not less than 80° C. and less than 90° C. for 23 hr or more, or not less than 90° C. and not more than 100° C. for 16 hr or more.

15. A method of producing the crystal according to claim 1, comprising neutralizing or acidifying an aqueous alkaline solution of 2-(3,4-dichlorobenzyl)-5-methyl-4-oxo-3,4-dihydrothieno[2,3-d]pyrimidine-6-carboxylic acid to provide an aqueous solution, and heating the aqueous suspension of 2-(3,4-dichlorobenzyl)-5-methyl-4-oxo-3,4-dihydrothieno[2,3-d]pyrimidine-6-carboxylic acid at not less than 60° C. and less than 70° C. for 144 hr or more, not less than 70° C. and less than 80° C. for 25 hr or more, not less than 80° C. and less than 90° C. for 23 hr or more, or not less than 90° C. and not more than 100° C. for 16 hr or more.

* * * * *

UNITED STATES PATENT AND TRADEMARK OFFICE
CERTIFICATE OF CORRECTION

PATENT NO. : 9,006,253 B2  Page 1 of 1
APPLICATION NO. : 14/226505
DATED : April 14, 2015
INVENTOR(S) : Hayashi et al.

It is certified that error appears in the above-identified patent and that said Letters Patent is hereby corrected as shown below:

In the claims

Claim 1, column 21, line 25, "diffraction angles 20" should read "diffraction angles $2\theta$"

Signed and Sealed this
Fifth Day of January, 2016

Michelle K. Lee
*Director of the United States Patent and Trademark Office*